United States Patent

Gruber et al.

[11] Patent Number: 5,981,694
[45] Date of Patent: *Nov. 9, 1999

[54] MELT-STABLE LACTIDE POLYMER COMPOSITION AND PROCESS FOR MANUFACTURE THEREOF

[75] Inventors: Patrick Richard Gruber, St. Paul; Jeffrey John Kolstad, Wayzata; Eric Stanley Hall, Crystal; Robin Sue Eichen Conn, Minneapolis; Christopher M. Ryan, Chisago City, all of Minn.

[73] Assignee: Cargill, Incorporated, Minneapolis, Minn.

[ * ] Notice: This patent is subject to a terminal disclaimer.

[21] Appl. No.: 08/966,111

[22] Filed: Nov. 7, 1997

Related U.S. Application Data

[60] Continuation of application No. 08/627,790, Mar. 29, 1996, Pat. No. 5,763,564, which is a division of application No. 08/445,775, May 22, 1995, Pat. No. 5,539,081, which is a division of application No. 08/233,000, Apr. 25, 1994, Pat. No. 5,446,123, which is a continuation of application No. 07/955,690, Oct. 2, 1992, Pat. No. 5,338,822.

[51] Int. Cl.[6] .................................................. C08G 63/08
[52] U.S. Cl. .......................... 528/354; 528/355; 528/356; 528/357; 528/480; 528/503; 525/413; 525/415; 428/486
[58] Field of Search ..................................... 528/354, 355, 528/356, 357, 480, 503; 525/413, 415; 549/274; 428/486

[56] References Cited

U.S. PATENT DOCUMENTS 1,095,205  5/1914  Gruter et al. ............................ 549/274
1,849,107  3/1932  Moss ...................................... 528/361

(List continued on next page.)

FOREIGN PATENT DOCUMENTS 683673   2/1971  Canada .
923245   3/1973  Canada .
0314245  5/1989  European Pat. Off. .

(List continued on next page.)

OTHER PUBLICATIONS

W. Carothers, et al., *Studies of Polymerization and Ring Formation. X. The Reversible Polymerization of Six–membered Cyclic Esters*, American Chemical Society Journal, v. 54, pp. 761–772 (1932).

E. Filachione, et al., *Lactic Acid Derivatives as Plasticizers Esters of Polymeric Lactic Acid*, Bur. Agric. Ind. Chem., v. 11, pp. 1–11 (1951).

D. Deanne and E. Hammond, *Coagulation of Milk for Cheese–Making by Ester Hydrolysis*, Journal of Diary Science, v. 43, pp. 1421–1429 (1960).

(List continued on next page.)

*Primary Examiner*—Duc Truong
*Attorney, Agent, or Firm*—Merchant, Gould, Smith, Edell, Welter & Schmidt, P.A.

[57] ABSTRACT

A lactide polymer composition combining compositional and purity limitations and catalyst optimization or addition of stabilizing agents resulting in a melt-stable polymer is disclosed. The melt-stable lactide polymer comprises a plurality of polylactide polymer chains, residual lactide in concentration of less than 2 percent and water in concentration of less than 1000 parts-per-million. A stabilizing agent in an amount sufficient to reduce depolymerization of the lactide polymer during melt-processing or alternatively, control of catalyst level at a molar ratio of monomer to catalyst greater than 3000:1 is also included in the melt-stable composition. A process for manufacture of a melt-stable lactide polymer composition includes polymerizing a lactide mixture and adding stabilizing agents sufficient to reduce depolymerization of the polylactide during melt-processing, followed by devolatilizing the polylactide to remove monomer and water.

24 Claims, 2 Drawing Sheets

U.S. PATENT DOCUMENTS

| | | | |
|---|---|---|---|
| 1,995,970 | 4/1935 | Dorough | 528/361 |
| 2,396,994 | 3/1946 | Filachione et al. | 560/179 |
| 2,703,316 | 3/1955 | Schneider | 528/354 |
| 2,758,987 | 8/1956 | Salzberg | 528/354 |
| 2,951,828 | 9/1960 | Zeile et al. | 528/57 |
| 3,268,487 | 8/1966 | Klootwijik | 528/355 |
| 3,332,791 | 7/1967 | Selman | 549/274 |
| 3,531,561 | 9/1970 | Trehu | 264/210 |
| 3,636,956 | 1/1972 | Schneider | 128/335.5 |
| 3,772,420 | 11/1973 | Glick et al. | 264/102 |
| 3,773,919 | 11/1973 | Boswell et al. | 424/19 |
| 3,839,297 | 10/1974 | Wassermann et al. | 528/357 |
| 3,887,699 | 6/1975 | Yolles | 424/19 |
| 4,045,418 | 8/1977 | Sinclair | 528/357 |
| 4,273,920 | 6/1981 | Nevin | 528/361 |
| 4,279,249 | 7/1981 | Vert et al. | 128/92 |
| 4,595,713 | 6/1986 | St. John | 523/105 |
| 4,643,734 | 2/1987 | Lin | 623/16 |
| 4,677,191 | 6/1987 | Tanaka et al. | 528/361 |
| 4,683,288 | 7/1987 | Tanaka et al. | 528/361 |
| 4,719,246 | 1/1988 | Murdoch et al. | 521/134 |
| 4,727,163 | 2/1988 | Bellis | 549/134 |
| 4,728,721 | 3/1988 | Yamamoto et al. | 528/361 |
| 4,766,182 | 8/1988 | Murdoch et al. | 525/413 |
| 4,789,726 | 12/1988 | Hutchinson | 528/354 |
| 4,797,468 | 1/1989 | DeVries | 528/254 |
| 4,800,219 | 1/1989 | Murdoch et al. | 525/413 |
| 4,835,293 | 5/1989 | Bhatia | 549/274 |
| 4,902,515 | 2/1990 | Loomis et al. | 424/486 |
| 4,950,258 | 8/1990 | Kawai et al. | 604/281 |
| 4,960,866 | 10/1990 | Bendix et al. | 528/499 |
| 4,981,696 | 1/1991 | Loomis et al. | 424/486 |
| 4,983,745 | 1/1991 | Muller et al. | 549/274 |
| 5,023,349 | 6/1991 | Bhatia | 549/274 |
| 5,023,350 | 6/1991 | Bhatia | 549/274 |
| 5,041,529 | 8/1991 | Shinoda et al. | 528/354 |
| 5,043,458 | 8/1991 | Bhatia | 549/274 |
| 5,053,485 | 10/1991 | Nieuwenhuis et al. | 528/354 |
| 5,053,522 | 10/1991 | Muller | 549/274 |
| 5,076,983 | 12/1991 | Loomis et al. | 264/101 |
| 5,108,399 | 4/1992 | Eitenmuller et al. | 606/77 |
| 5,124,023 | 6/1992 | Gruber et al. | 528/354 |
| 5,132,397 | 7/1992 | DeGuia . | |
| 5,136,017 | 8/1992 | Kharas et al. | 528/354 |
| 5,252,646 | 10/1993 | Iovine et al. . | |
| 5,302,694 | 4/1994 | Buchholz . | |
| 5,338,822 | 8/1994 | Gruber et al. | 528/354 |
| 5,539,081 | 7/1996 | Gruber et al. . | |
| 5,763,564 | 6/1998 | Gruber et al. | 528/354 |

FOREIGN PATENT DOCUMENTS

| | | |
|---|---|---|
| 267826 | 12/1913 | Germany . |
| 1083275 | 12/1960 | Germany . |
| 1543958 | 2/1970 | Germany . |
| 3632103 | 3/1988 | Germany . |
| 43-002949 | 2/1968 | Japan . |
| 43-003017 | 2/1968 | Japan . |
| 43-008614 | 4/1968 | Japan . |
| 1040168 | 8/1966 | United Kingdom . |
| 1108720 | 4/1968 | United Kingdom . |
| 808731 | 3/1969 | United Kingdom . |
| 1161932 | 8/1969 | United Kingdom . |
| WO90/01521 | 2/1990 | WIPO . |
| WO91/02015 | 2/1991 | WIPO . |
| WO91/06601 | 5/1991 | WIPO . |
| WO92/00292 | 1/1992 | WIPO . |
| WO92/04413 | 3/1992 | WIPO . |
| WO92/05167 | 4/1992 | WIPO . |
| WO92/05168 | 4/1992 | WIPO . |
| PCT/US93/ 09330 | 2/1994 | WIPO . |

OTHER PUBLICATIONS

Kulkarni et al., *Biodegradable Poly(lactic acid) Polymers*, J. Biomed. Mater. Res., 5:619–181 (1971).

A. Schindler et al., *Biodegradable Polymers for Sustained Drug Delivery*, Contemporary Topics in Polymer Science 2:251–287 (1977).

I. Luderwald, *Thermal Degradation of Polyesters in the Mass Spectrometer*, Dev. Polymer Degradation 2:77–98 (1979).

M. Vert and F. Chabot, *Stereoregular Bioresorbable Polyesters for Orthopaedic Surgery*, Makromol Chem., Supp. 5, pp. 30–41 (1981).

M. Gupta and V. Deshmukh, *Thermal Oxidative Degradation of Poly–lactic Acid; Part I: Activation Energy of Thermal Degradation in Air*, Colloid & Polymer Science 260:308–311 (1982).

M. Gupta and V. Deshmukh, *Thermal Oxidative Degradation of Poly–lactic Acid; Part II: Molecular Weight and Electronic Spectra During Isothermal Heating*, Colloid & Polymer Science 260:514–417 (1982).

G. Van Hummel and S. Harkema, *Structure of 3.6–Dimethyl–1,4–Dioxane–2.5–Dione [D–,D–{L–,L–}Lactide]*, Acta. Crystallogr. B38:1679–1981 (1982).

F. Chabot et al., *Configuration Structures of Lactic Acid Stereocopolymers as Determined by $^{13}C(^{1}H)$ N.M.R.*, Polymer 24:53–59 (1983).

F. Kohn et al., *The Ring–Opening Polymerization of D,L–Lactide in the Melt Initiated with Tetraphenyltin*, Journal of Applied Polymer Science 29:4265–4277 (1984).

H. Kricheldorf and A. Serra, *Polylactones 6. Influence of Various Metal Salts on the Optical Purity of Poly(L–lactide)*, Polymer Bulletin 14:497–502 (1985).

A. Chawla and T. Chang, *In–Vivo Degradation of Poly(lactic acid) of Different Molecular Weights*, Biomat., Med. Dev., Art. Org., 13:153–162 (1985).

I. McNeill and H. Leiper, *Degradation Studies of Some Polyesters and Polycarbonates—1. Polyactide: General Features of the Degradation Under Programmed Heating Conditions*, Polymer Degradation and Stability 11:267–285 (1985).

I. McNeill and H. Leiper, *Degradation Studies of Some Polyesters and Polycarbonates—2. Polylactide: Degradation Under Isothermal Conditions, Thermal Degradation Mechanism and Photolysis of the Polymer*, Polymer Degradation and Stability 11:309–326 (1985).

Makino et al., *Preparation and in Vitro Degradation Properties of Polyactide Microcapsules*, Chem. Pharm. Bull. 33:1195–1201 (1985).

D. Garozzo et al., *Primary Thermal Decomposition Processes in Aliphatic Polyesters Investigated by Chemical Ionization Mass Spectrometry*, Macromolecules 19:1643–1649 (1986).

*Irganox® 1076 Antioxidant and Thermal Stabilizer*, (published on an unknown date in 1986 by Ciba–Geigy Corporation, Three Skyline Drive, Hawthorne, NY 10532).

Nakamura et al., *Surgical Application of Biodegradable Films Prepared from Lactide–ε–Caprolactone Copolymers*, Bio. Materials and Clinical Applications 7:759–764 (1987).

H. Kricheldorf et al., *Polymerization Mechanism of Metal Alkoxide Initiated Polymerizations of Lactide and Various Lactones*, Makromol. 21:286–293 (1988).

K. Jamshidi et al., *Thermal Characterization of Polylactides*, Polymer 29:2229–2234 (1988).

M. Vert, *Bioresorbable Polymers for Temporary Therapeutic Applicaions*, Die Angwandte Makromolekulare Chemie 166–167:155–168 (1989).

*Hydrolytic Stability/Corrosivity of Phosphite Costabilizers*, (Technical Bulletin 89–04, published on an unknown date in 1989, by Stars Laboratory, Additives Division, Ciba–Geigy Corporation, Ardsley, NY 10502).

*GE Specialty Chemicals Product Guide CA–4001E*, (published on an unknown date in 1989, by General Electric Company, 5th and Avery Street, Parkersburg, WV 26102).

*Tinuvin® 123 Hindered Aminoether Light Stabilizer for Coatings*, (published on an unknown date in 1989, by Ciba–Geigy Corporation, Three Skyline Drive, Hawthorne, NY 10523).

*Irganox® B–Blends Antioxidents and Process Stabilizers for Polymers*, (published on an unknown date in Mar., 1990 by Ciba–Geigy Corporation, Three Skyline Drive, Hawthorne, NY 10523).

*Naugard® 445, Specialty Chemicals*, (a product brochure published on or before May 1, 1990, by Uniroyal Chemical Company, Inc., Middlebury, CT 06749).

*Ethanox® 393 Antioxidant, The First Fluorophosphonite Antioxident*, (published on or before an unknown date in Oct., 1990, by Ethyl Corporation, 451 Florida Blvd., Baton Rouge, LA 70801).

*The Resomer® Resorable Polyesters*, (published on or before an unknown date in Feb., 1991 by Boehringer Ingelheim KG, D–6507 Ingelheim, W. Germany).

P. Klemchuk, *Introduction to Polymer Degradation*, lecture notes distributed at a seminar entitled Priciples of Polymer Degradation and Stabilization in Orlando, Florida, Oct. 28–30, 1991, sponsored by The Institute of Materials Science, State University of New York and New Paltz.

R. Thomas, *Degradation and Stabilization of Engineering Polymers*, lecture notes distributed at a seminar entitled: Principles of Polymer Degradation and Stabilization in Orlando, Florida, Oct. 28–30, 1991, sponsored by the Institute of Materials Science, State University of New York at New Paltz.

W. Enlow, *Process Stabilization with Phosphite Antioxidants*, lecture notes distributed at a seminar entitled: Principles of Polymer Degradation and Stabilization in Orlando, Florida, Oct. 28–30, 1991, sponsored by The Intitute of Materials Science, State University of New York at New Paltz.

*Naugard® XL–1 Specialty Chemicals*, (product brochure published on an unknown date in Feb., 1992, by Uniroyal Chemical Co., Inc., Middlebury, CT 06749).

Sir John Meurig Thomas, *Solid Acid Catalyst*, Scientific American, pp. 112–118 (Apr. 1992).

*Argus Product Data, Argus® Dimyristyl Thiodipropinate*, (published on or before an unknown date in Aug. 1992 by Argus Division, Witco Corporation, 633 Court Street, Brooklyn, NY 11231–2193).

*Argus Thiochemical Product Data, Argus® Thiodipropionate*, (published on or before and unknown date in Aug., 1992, by Argus Division, Witco Corporation, 633 Court Street, Brooklyn, NY 11231–2193).

*Argus Product Data, Argus® Distearyl Thiodipropionate*, (published on or before an unknown date in Aug., 1992, by Argus Division, Witco Corporation, 633 Court Street, Brooklyn, NY 11231–2193).

*Argus Product Data, Mark® 2140 Pentaery Octylthiopropionate*, (published on or before an unknown date in Aug., 1992, by Argus Division, Witco Corporation, 633 Court Street, Brooklyn, NY 11231–2193).

*Argus Thiochemical Product Data, Argus® Dilauryl Thiodipropionate*, (published on or before an unknown date in Aug., 1992, by Argus Division, Witco Corporation, 633 Court Street, Brooklyn, NY 11231–2193).

*Argus Product Data, Seenox® 412S Pentaerythritol Tetrakas (B–Laurylthiopropionate*, (published on or before an unknown date in Aug., 1992, by Argus Division, Witco Corporation, 633 Court Street, Brooklyn, NY 11231–2193).

*Irganox® 1010*, (a product brochure published on or before an unknown date in Aug., 1992, by Ciba–Geigy Corporation, Three Skyline Drive, Hawthorne, NY 10532).

*Irganox® MD 1024, Metal Deactivator/Antioxidant*, (published on an unknown date prior to Aug., 1992, by Ciba–Geigy Corporation, Three Skyline Drive, Hawthorne, NY 10532).

*Tinuvin® 622LD Low Dust, Hindered Amine Light Stabilizer for Polymers FDA–Cleared for Polyolefins*, (published on an unknown date before Aug., 1992, by Ciba–Geigy Corporation, Three Skyline Drive, Hawthorne, NY 10532).

T.M. Jackanicz, *Polyactic Acid as a Biodgradable Carrier for Contraceptive Steroids*, Contraception vol. 8, No. 3, 227–234 (1973).

A.D. Schwope, et al. *Lactic/Glycolic Acid Polymers as Narotic Antagonist Delivery Systems*, Life Sciences, vol. 17, 1877–1886 (1975).

L.C. Anderson, *An Injectable Sustained Release Fertility Control System*, Contraception, vol. 13, No. 3, 375–384 (1976).

D.L. Wise et al., *Sustained Release of an Antimalarial Drug Using a Copolymer of Glycolic/Lactic Acid*, Life Sciences, vol. 19, 867–874 (1976).

R.A. Miller et al., *Degradation Rates of Resorbable Implants (Polyactates and Polyglycolates): Rate Modification with Changes in Pla/Pga Copolymer Rations*, J. Biomed. Mater. Res., vol. 11, 711–719 (1977).

D.K. Gilding et al., *Biodegradable Polymers for Use in Surgery—Polyglycolic/Polylactic Acid Homo and Copolymers: 1.*, Polymer, vol. 2, 1459–1464 (1979).

D.K. Gilding, *Degradation of Polymers: Mechanisms and Implications for Biomedical Applications, Biocompatibility of Clinical Implant Materials*, D.F. Williams, edl., vol. 1, 43–65 (1981).

A.M. Reed and D.K. Gilding, *Biodegradable Polymers for Use in Surgery Polyglycolic/Polylactic Acid Homo and Copolymers: 2. In Vitro Degradation*, Polymer, vol. 22, No. 4, 494–498 (1981).

D.K. Gilding, *Biodegradable Polymers*, Biocompatibility of Clincal Implant Materials, D.F. Williams, ed., Vol. 2, 209–232 (1981).

J.D. Strobel, *Biodegradable Polymers*, paper presented at Medical Textiles and Biomedical Polymers and Materials Conference held at Clemson, S.C., U.S.A., Dec. 5–6, 1989, Stolle Research and Development Corp., PD 712–01, pp. 1–32 and attachments A1–A21.

*Biocompatable Composite Would be Completely Absorbed in the Body*, Advanced Materials, vol. 12, No. 15, Aug. 1990, p. 6.

*Polyactides Exhibit Degradability*, Tappai Journal, Sep. 1991, p. 42.

P.V. Bonsignore et al., 1992, *Poly(lactic acid) Degradable Plastics, Coatings, and Binders*, TAPPI Proceedings (Nonwovens Conference); pp. 129–140.

MELT-STABLE LACTIDE POLYMER COMPOSITION AND PROCESS FOR MANUFACTURE THEREOF

CROSS REFERENCE TO RELATED APPLICATIONS

This application is a Continuation of application Ser. No. 08/627,790, filed Mar. 29, 1996, and which issued as U.S. Pat. No. 5,763,564. Application Ser. No. 08/627,790 is a Divisional of application Ser. No. 08/445,775, filed May 22, 1995, and which issued as U.S. Pat. No. 5,539,081. Application Ser. No. 08/445,775 is a Divisional of application Ser. No. 08/233,000, filed Apr. 25, 1994, which issued as U.S. Pat. No. 5,446,123. Application Ser. No. 08/233,000 is a Continuation of application Ser. No. 07/955,690, filed Oct. 2, 1992, which issued as U.S. Pat. No. 5,338,822. These applications and patents are incorporated herein by reference.

BACKGROUND OF THE INVENTION

1. Field of the Invention

The present invention relates to a melt-stable lactide polymer composition and a process for manufacturing such composition from lactide in the field of degradable polymers.

2. Description of the Prior Art

The continued depletion of landfill space and the problems associated with incineration of waste have led to the need for development of truly biodegradable polymers to be utilized as substitutes for non-biodegradable or partially biodegradable petrochemical-based polymers. The use of lactic acid and lactide to manufacture a biodegradable polymer is well-known in the medical industry. As disclosed by Nieuwenhuis et al. (U.S. Pat. No. 5,053,485), such polymers have been used for making biodegradable sutures, clamps, bone plates and biologically active controlled release devices. Processes developed for the manufacture of polymers to be utilized in the medical industry have incorporated techniques which respond to the need for high purity and biocompatability in the final product. These processes were designed to produce small volumes of high dollar-value products, with less emphasis on manufacturing cost and yield.

In order to meet projected needs for biodegradable packaging materials, others have endeavored to optimize lactide polymer processing systems. Gruber et al. (U.S. Pat. No. 5,142,023) disclose a continuous process for the manufacture of lactide polymers with controlled optical purity from lactic acid having physical properties suitable for replacing present petrochemical-based polymers for packaging, paper-coating and other non-medical industry applications.

Generally, manufacturers of polymers utilizing processes such as those disclosed by Gruber et al. will convert raw material monomers into polymer beads, resins or other pelletized or powdered products. The polymer in this form is then sold to end users who extrude, blow-mold, cast films, blow films, thermoform, injection-mold or fiber-spin the polymer at elevated temperatures to form useful articles. The above processes are collectively referred to as melt-processing. Polymers produced by processes such as those disclosed by Gruber et al., which are to be sold commercially as beads, resins, powders or other non-finished solid forms are generally referred to collectively as polymer resins.

Prior to the present invention, it is believed that there has been no disclosure of a combination of composition control requirements which will lead to the production of commercially viable lactide polymer resins for the melt-processors.

It is generally known that lactide polymers or polylactide are unstable. The concept of instability though, has both negative and positive aspects. The positive aspect is the biodegradation or other forms of degradation to form non-hazardous products when lactide polymers or articles manufactured from lactide polymers are discarded or composted after completing their useful life. The negative aspect of such instability is the degradation of lactide polymers during processing at elevated temperatures as, for example, during melt-processing by end-user purchasers of polymer resins. Thus, the same properties that make lactide polymers desirable as replacements for non-degradable petrochemical polymers also creates undesirable effects during processing which must be overcome.

Lactide polymer degradation at elevated temperature has been the subject of several studies, including: I. C. McNeill and H. A. Leiper, *Polymer Degradation and Stability*, vol. 11, pp. 267–285 (1985); I. C. McNeill and H. A. Leiper, *Polymer Degradation and Stability*, vol. 11, pp. 309–326 (1985); M. C. Gupta and V. G. Deshmukh, *Colloid & Polymer Science*, vol. 260, pp. 308–311 (1982); M. C. Gupta and V. G. Deshmukh, *Colloid & Polymer Science*, vol. 260, pp. 514–517 (1982); Ingo Luderwald, *Dev. Polymer Degradation*, vol. 2, pp. 77–98 (1979); Domenico Garozzo, Mario Giuffrida, and Giorgio Montaudo, *Macromolecules*, vol. 19, pp. 1643–1649 (1986); and, K. Jamshidi, S. H. Hyon and Y. Ikada, *Polymer*, vol. 29, pp. 2229–2234 (1988).

It is known that lactide polymers exhibit an equilibrium relationship with lactide as represented by the reaction below:

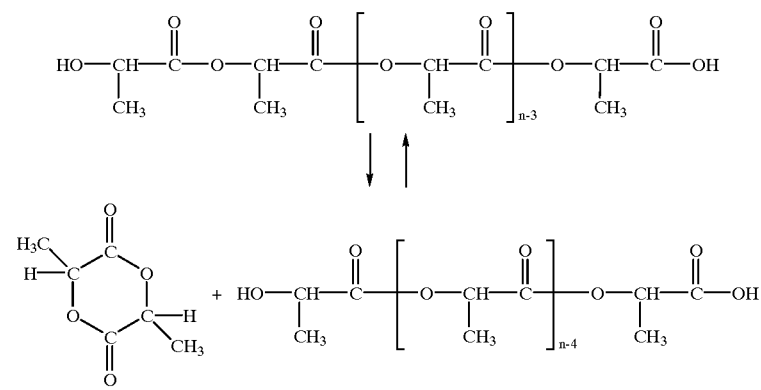

No consensus has been reached as to what the primary degradation pathways are at elevated processing temperatures. One of the proposed reaction pathways includes the reaction of a hydroxyl end group in a "back-biting" reaction to form lactide. This equilibrium-reaction is illustrated above. Other proposed reaction pathways include: reaction of the hydroxyl end group in a "back-biting" reaction to form cyclic oligomers, chain scission through hydrolysis of the ester bonds, an intramolecular beta-elimination reaction producing a new acid end group and an unsaturated carbon-carbon bond, and radical chain decomposition reactions. Regardless of the mechanism or mechanisms involved, the fact that substantial degradation occurs at elevated temperatures, such as those used by melt-processors, creates an obstacle to use of lactide polymers as a replacement for petrochemical-based polymers. It is apparent that degradation of the polymer during melt-processing must be reduced to a commercially acceptable rate while the polymer maintains the qualities of biodegradation or compostability which make it so desirable. It is believed this problem has not been addressed prior to the developments disclosed herein.

As indicated above, polylactides have been produced in the past, but primarily for use in medical devices. These polymers exhibit biodegradability, but also a more stringent requirement of being bioresorbable or biocompatible. As disclosed by M. Vert, *Die Ingwandte Makromolekulare Chemie*, vol. 166–167, pp. 155–168 (1989), "The use of additives is precluded because they can leach out easily in body fluids and then be recognized as toxic, or, at least, they can be the source of fast aging with loss of the properties which motivated their use. Therefore, it is much more suitable to achieve property adjustment through chemical or physical structure factors, even if aging is still a problem." Thus, work aimed at the bioresorbable or biocompatible market focused on polylactide and blends which did not include any additives.

Other disclosures in the medical area include Nieuwenhuis (European Patent No. 0 314 245), Nieuwenhuis (U.S. Pat. No. 5,053,485), Eitenmuller (U.S. Pat. No. 5,108,399), Shinoda (U.S. Pat. No. 5,041,529), Fouty (Canadian Patent No. 808,731), Fouty (Canadian Patent No. 923,245), Schneider (Canadian Patent No. 863,673), and Nakamura et al., *Bio. Materials and Clinical Applications*, Vol. 7, p. 759 (1987). As disclosed in these references, in the high value, low volume medical specialty market, polylactide or lactide polymers and copolymers can be given the required physical properties by generating lactide of very high purity by means of such methods as solvent extraction and recrystallization followed by polymerization. The polymer generated from this high purity lactide is a very high molecular weight product which will retain its physical properties even if substantial degradation occurs and the molecular weight drops significantly during processing. Also, the polymer may be precipitated from a solvent in order to remove residual monomer and catalysts. Each of these-treatments add stability to the polymer, but clearly at a high cost which would not be feasible for lactide polymer compositions which are to be used to replace inexpensive petrochemical-based polymers in packaging, paper-coating and other non-medical applications.

Furthermore, it is well-known that an increase in molecular weight generally results in an increase in a polymer's viscosity. A viscosity which is too high, can prevent melt-processing of the polymer due to physical/mechanical limitations of the melt-processing equipment. Melt-processing of higher molecular weight polymers generally requires the use of increased temperatures to sufficiently reduce viscosity so that processing can proceed. However, there is an upper limit to temperatures used during processing. Increased temperatures increase degradation of the lactide polymer, as the previously-cited studies disclose.

Jamshidi et al., *Polymer*, Vol. 29, pp. 2229–2234 (1988) disclose that the glass transition temperature of a lactide polymer, $T_g$, plateaus at about 57° C. for polylactide having a number average molecular weight of greater than 10,000. It is also disclosed that the melting point, $T_m$, levels off at about 184° C. for lactide polymers having a number average molecular weight of about 70,000 or higher. This indicates that at a relatively low molecular weight, at least some physical properties of lactide polymers plateau and remain constant.

Sinclair et al. (PCT Application No. WO 92/04413) disclose the use of residual monomer, lactic acid or lactic acid oligomers to plasticize polylactide polymers, with plasticizer levels of 2–60%. Loomis (U.S. Pat. No. 5,076,983) discloses a process for manufacturing a self-supporting film in which the oligomers of hydroxy acids are used as plasticizing agents. Loomis and Sinclair et al. disclose that the use of a plasticizer such as lactide or lactic acid is beneficial to produce more flexible materials which are considered to be preferable. Sinclair et al., however, disclose that residual monomer can deposit out on rollers during processing. Loomis also recognizes that excessive levels of plasticizer can cause unevenness in films and may separate and stick to and foul drums used for casting such films. Thus, plasticizing as recommended, negatively impacts melt-processability.

Accordingly, a need exists for a lactide polymer composition which is melt-stable under the elevated temperatures common to melt-processing. The needed melt-stable polymer composition must also exhibit sufficient compostability or degradability after its useful life in order to be manufactured into useful polymeric articles which are suitable as cost-competitive replacements for similar articles made of petrochemical-based polymers. Further, the melt-stable polymer must be processable in existing melt-processing equipment, by exhibiting sufficiently low viscosities at melt-processing temperatures while polymer degradation remains below a point of substantial degradation and does not cause excessive fouling of processing equipment. Furthermore, the polymer lactide must retain its molecular weight, viscosity and other physical properties within commercially-acceptable levels through melt-processing. It will be further appreciated that a need also exists for a process for manufacturing such polymer compositions. The present invention addresses these needs as well as other problems associated with existing lactide polymer compositions and manufacturing processes therefor. The present invention also offers further advantages over the prior art, and solves other problems associated therewith.

SUMMARY OF THE INVENTION

According to the present invention, a melt-stable lactide polymer composition is provided, preferably a generally amorphous melt-stable lactide polymer composition comprising: a plurality of polylactide polymer chains preferably having a number average molecular weight of from about 10,000 to about 300,000; lactide in a concentration of less than about 2 percent by weight; water in a concentration of less than about 1,000 parts-per-million; and a stabilizing agent in an amount sufficient to reduce depolymerization of the polylactide polymer chains during melt-processing to less than 2 percent. A process for the manufacture of a melt-stable lactide polymer composition is also provided.

As previously disclosed, it is recognized in the art that polymers of lactide degrade under conditions of elevated temperature. It is also recognized that commercially, a manufacturer of lactide polymers utilizing a lactide monomer mixture as a raw material will usually produce a lactide polymer resin to be sold to end users or processors. The end user or processor will purchase the resin and, in most instances, melt-process the resin to produce useful articles such as thin films, packaging materials, coated papers, non-woven articles and any other useful article that may be molded or extruded from the resin. It is recognized however, that the polymer manufacturer may also melt-process and sell the finished articles.

It is recognized that the exact method of melt-processing is not relevant to the invention disclosed herein. Rather it is only necessary to recognize that the purchaser/processor of polymer resin must necessarily process the resin at elevated temperature, i.e., melt-process. Melt-processing of the resin compositions of the present invention would, in most instances, be processable in existing melt-processing equipment which is used to process petrochemical-based resins. The purchased lactide polymer resin must be sufficiently stable through melt-processing (reduced degradation) to give predictable and relatively constant physical properties within the resulting product. Further, the resin must not degrade and produce excessive by-products which foul process equipment.

Applicants have found that processability in existing melt-process equipment generally requires that the molecular weight of the resin be low enough so that the viscosity is low enough at melt-processing temperatures which do not cause substantial degradation. The lower viscosity allows existing equipment to mechanically process the resin. Reduced degradation prevents fouling while maintaining physical properties. This includes maintaining the initial molecular weight and viscosity through melt-processing to avoid changes in physical properties. Thus, the requirement of processability is that the resin is sufficiently stable that decomposition or degradation by-products do not cause substantial fouling or plating out on existing equipment. As to physical properties of the polymer subsequent to melt-processing, the end user or melt-processor must be able to rely on the consistency of the resin to give relatively constant tensile strength, percent elongation at break, impact strength, modulus of elasticity, flexural modulus, yield and flexural strength.

As disclosed herein, Applicants have developed compositional requirements and methods of manufacture which address the needs of the end user or melt-processor. The resulting resin or lactide polymer composition of the present invention is referred to generally as a melt-stable lactide polymer. A melt-stable lactide polymer is a polymer which has viscosity low enough at melt-processing temperatures to be processed in existing or commercially-available melt-processing equipment and have sufficiently low rates of degradation so that at the same temperatures the amount of degradation during processing does not substantially affect the physical properties of the final polymeric article or cause significant plating or fouling on processing equipment. These physical properties include molecular weight and viscosity as well as others disclosed herein. A test of melt stability would include heating a devolatilized sample of lactide polymer to 180° C. at atmospheric pressure and measuring the percent by weight generation of lactide in the first hour. In a preferred composition of the present melt-stable lactide polymers, the amount of lactide generation is less than 3 percent by weight, preferably less than 2 percent by weight and most preferably less than 1 percent by weight in the first hour.

The melt-stable lactide polymer compositions of the present invention comprise a plurality of polylactide polymer chains having a number average molecular weight from about 10,000 to about 300,000. In a preferred composition, the number average molecular weight ranges from about 15,000 to about 150,000. The melt-stable lactide polymer composition preferably is the reaction product of polymerizing a lactide mixture comprising about 5 percent by weight to about 50 percent by weight meso-lactide and about 95 percent by weight or less L-lactide. With this preferred optical composition, the resulting melt-stable lactide polymer is generally amorphous.

The residual monomer concentration in the melt-stable lactide polymer composition is less than 2 percent by weight. The residual monomer is generally lactide although lactic acid and other oligomers of lactic acid, both cyclic and linear may be present as decomposition by-products or residual contaminants from the polymerization reaction. In a preferred composition, the concentration of lactide in the polymer is less than 0.5 percent by weight. Contrary to previous disclosures, Applicants have found that the monomer cannot be used as a plasticizing agent in the resin of the present invention due to significant fouling or plating out problems in processing equipment. Thus, the residual monomer concentration must be held below 2 percent by weight and preferably below 1 percent by weight and most preferably less than 0.2 percent by weight. It is believed that at these low levels the residual monomer does not act as a plasticizer.

The water concentration within the melt stable lactide polymer composition is less than about 1,000 parts-per-million by weight. Applicants have found that the presence of water in greater concentration causes excessive loss of molecular weight and generation of decomposition by-products which affect the physical properties of the melt-processed polymer.

In a preferred composition, a stabilizing agent in an amount sufficient to reduce depolymerization of the polylactide polymer during melt-processing to less than about 2 percent by weight generation of lactide in the first hour at 180° C. in atmospheric pressure is included in the melt-stable lactide polymer composition (a devolatilized sample is used to test melt-stability). In preferred compositions the rate of generation is less than 1.5 percent by weight and more preferably, less than 1.0 percent by weight generation of lactide during the first hour at 180° C. and atmospheric pressure.

The stabilizing agents may include antioxidants and/or water scavengers. Preferable antioxidants are phosphite-containing compounds, hindered phenolic compounds or other phenolic compounds. Antioxidants include such compounds as trialkyl phosphites, mixed alkyl/aryl phosphates, alkylated aryl phosphites, sterically hindered aryl phosphites, aliphatic spirocyclic phosphites, sterically hindered phenyl spirocyclics, sterically hindered bisphosphonites, hydroxyphenyl propionates, hydroxy benzyls, alkylidene bisphenols, alkyl phenols, aromatic amines, thioethers, hindered amines, hydroquinones and mixtures thereof.

The water scavengers which may be utilized in preferred embodiments of the melt-stable lactide polymer composition include: carbodiimides, anhydrides, acyl chlorides, isocyanates, alkoxy silanes, and desiccant materials such as clay, alumina, silica gel, zeolites, calcium chloride, calcium carbonate, sodium sulfate, bicarbonates or any other compound which ties up water. Preferably the water scavenger is degradable or compostable.

In the manufacture of the melt-stable lactide polymer compositions of the present invention, the reaction to polymerize lactide is catalyzed. Many catalysts have been cited in literature for use in the ring-opening polymerization of lactones. These include but are not limited to: $SnCl_2$, $SnBr_2$, $SnCl_4$, $SnBr_4$, aluminum alkoxides, tin alkoxides, zinc alkoxides, SnO, PbO, Sn (2-ethyl hexanoates), Sb (2-ethyl hexanoates), Bi (2-ethyl hexanoates), Na (2-ethyl hexanoates) (sometimes called octoates), Ca stearate, Mg stearate, Zn stearate, and tetraphenyltin. Applicants have tested several catalysts for polymerization of lactide at 180° C., which include: tin(II) bis(2-ethyl hexanoate) [T-9, Atochem], dibutyltin diacetate [Fascat 4200®, Atochem], butyltin tris(2-ethyl hexanoate) [Fascat 9102®, Atochem], hydrated monobutyltin oxide [Fascat 9100®, Atochem], antimony triacetate [S-21, Atochem], and antimony tris (ethylene glycoxide) [S-24, Atochem]. Of these catalysts, tin(II) bis(2-ethyl hexanoate), butyltin tris (2-ethyl hexanoate) and dibutyltin diacetate appear to be most effective.

Applicants have found the use of catalysts to polymerize lactide significantly affects the stability of the resin product. It appears the catalyst also is effective at catalyzing the reverse depolymerization reaction. To minimize this negative effect, in a preferred composition, the residual catalyst level in the resin is present in a molar ratio of monomer-to-catalyst greater than 3000:1, preferably greater than 5,000:1 and most preferably greater than 10,000:1. Applicants believe ratios as high as 20,000:1 could also be utilized, however, polymerization time would be long. Applicants have found that when catalyst level is controlled within these parameters, catalytic activity is sufficient to polymerize the lactide while sufficiently low to enable melt-processing without adverse effect when coupled with low residual monomer level and low water concentration, as described above, in polymers of molecular weight between about 10,000 to about 300,000.

Applicants have also found that catalyst concentration may be reduced subsequent to polymerization by precipitation from a solvent. This produces a resin with reduced catalyst concentration. In an alternative embodiment, the catalyst means for catalyzing the polymerization of lactide to form the polylactide polymer chains which was incorporated into the melt-stable lactide polymer composition during polymerization is deactivated by including in the melt-stable lactide polymer composition a catalyst deactivating agent in amounts sufficient to reduce catalytic depolymerization of the polylactide polymer chains. Such catalyst-deactivating agents include, but are not limited to, hindered alkyl, aryl and phenolic hydrazides, amides of aliphatic and aromatic mono- and dicarboxylic acids, cyclic amides, hydrazones and bishydrazones of aliphatic and aromatic aldehydes, hydrazides of aliphatic and aromatic mono- and dicarboxylic acids, bis-acylated hydrazine derivatives, heterocyclic compounds and mixtures thereof.

The preferred melt-stable lactide polymer composition is the reaction product of polymerization of lactide at a temperature greater than about 160° C. Applicants have found that polymerization at higher temperatures results in a characteristically different polymer which is believed to have higher melt stability and viscosity due to increased transesterification during polymerization.

The process for manufacture of a melt-stable lactide polymer comprises the steps of first providing a lactide mixture wherein the mixture contains about 5 percent by weight to about 50 percent by weight meso-lactide and about 95 percent by weight or less L-lactide. This mixture is polymerized to form polylactide and unreacted monomer in the presence of a catalyst means for catalyzing the polymerization of lactide to form polylactide. A stabilizing agent, as disclosed above, may be added simultaneously with or prior to the polymerizing of the lactide to form polylactide. The stabilizing agent may also be added subsequent to polymerization. As previously disclosed, the stabilizing agent is added in a sufficient amount to reduce depolymerization of a devolatilized polylactide sample during melt-processing to less than 2 percent by weight generation of lactide in the first hour at 180° C. and atmospheric pressure. Preferably, lactide generation is less than 1.5 percent by weight, more preferably, less than 1.0 percent by weight. The lactide polymer is devolatilized to remove unreacted monomer which may also be a by-product of decomposition reactions and residual water which may be present. Applicants recognize that the catalyst used to polymerize lactide may be in the form of a soluble catalyst or an insoluble solid, supported catalyst. The process, preferably, also includes the step of adding a molecular weight control agent to the lactide prior to catalyzing the polymerization of the lactide. Molecular weight control agents include active hydrogen-bearing compounds such as lactic acid, esters of lactic acid, alcohols, amines, glycols, diols, and triols which function as chain-initiating agents. Such molecular weight control agents are added in sufficient quantity to control the number average molecular weight of the polylactide to between about 10,000 and about 300,000, in preferred embodiments.

In a preferred process of the present invention, the step of devolatilizing includes at least reducing the concentration of unreacted lactide to less than about 2 percent by weight and the concentration of water to less than about 1,000 parts-per-million. Preferably, the lactide concentration is reduced to less than 1 percent by weight and more preferably less than 0.2 percent by weight.

These and various other advantages and features of novelty which characterize the present invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there are illustrated and described preferred embodiments of the present invention.

BRIEF DESCRIPTION OF THE DRAWINGS

In the drawings, in which like reference numerals indicate corresponding parts or elements of preferred embodiments of the present invention throughout the several views.

DETAILED DESCRIPTION OF THE PREFERRED EMBODIMENT(S)

Figure 1:
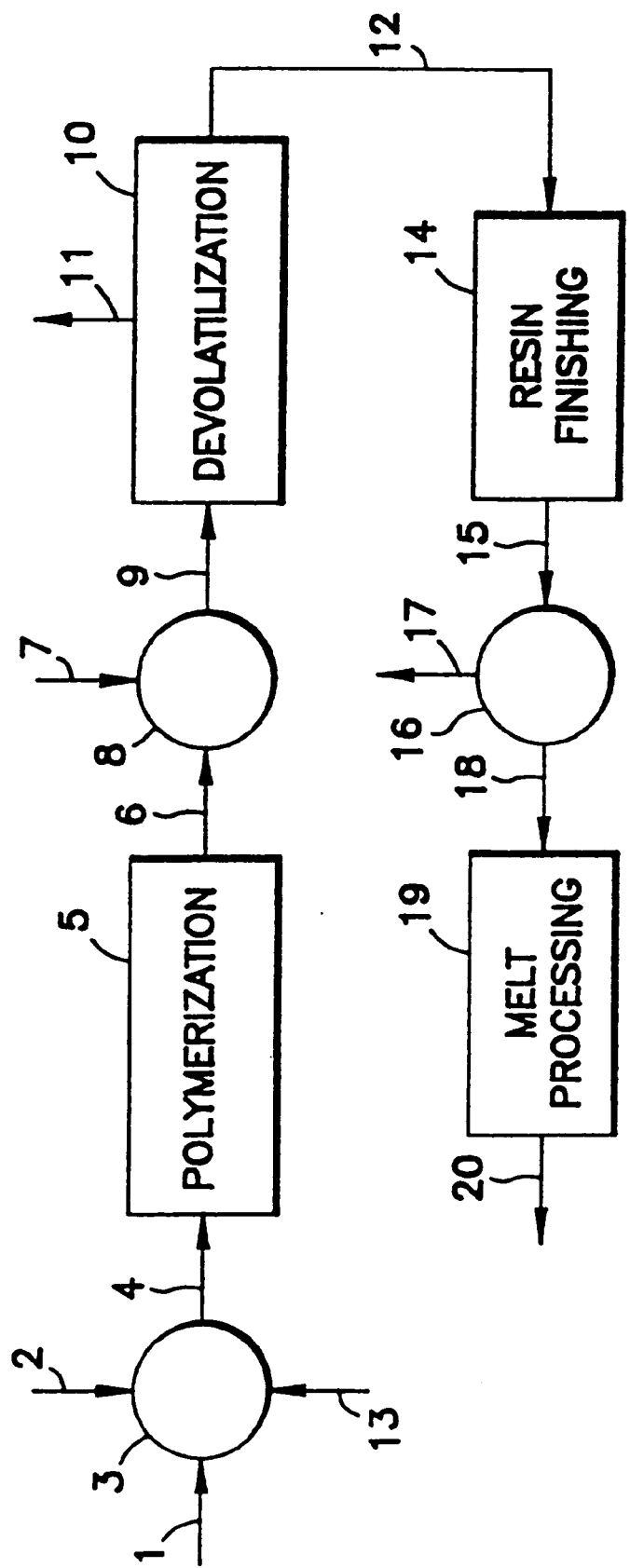
FIG. 1 is a schematic representation of a preferred process for the manufacture of a melt-stable lactide polymer composition.

As required, detailed embodiments of the present invention are disclosed herein. However, it is to be understood that the disclosed embodiments are merely exemplary of the present invention which may be embodied in various systems. Therefore, specific details disclosed herein are not to be interpreted as limiting, but rather as a basis for the claims and as a representative basis for teaching one skilled in the art to variously practice the present invention.

Lactide Polymers

Gruber et al. (U.S. Pat. No. 5,142,023) disclose a continuous process for the manufacture of lactide polymers with controlled optical purity from lactic acid, which is incorporated herein by reference. As disclosed by Gruber, the general route to producing a lactide polymer begins with either lactic acid or an ester of lactic acid which is first processed to form a purified lactide (the cyclic dimer). The lactide may vary in optical composition and levels of impurities. This purified lactide stream is then polymerized to form lactide polymer compositions utilized in the present invention. The lactide polymer compositions and process for manufacturing the lactide polymer compositions disclosed herein focus on meeting the requirements of the end user melt-processor of a lactide polymer resin such as that produced from a process disclosed by Gruber et al. As disclosed herein, the problems with degradation and fouling during melt-processing of lactide polymers are addressed through compositional limits on impurities such as residual monomer, water and catalyst along with the use of stabilizing agents and catalyst-deactivating agents.

In general, according to the present invention, a melt-stable lactide polymer and a process for manufacturing a melt-stable lactide polymer are disclosed. Lactide polymers are generally known and cited for their usefulness due to biodegradable properties. Furthermore, lactide polymers are compostable as illustrated in Example 9 below. Several mechanisms for each type of degradation have been proposed, however, there is no consensus as to which mechanisms are primary to the degradation of lactide polymers. Applicants believe the hydrolysis of the ester may be the key to or the first step in degradation of a lactide polymer composition. The mechanism of degradation is not key to the compositions of the present invention, however it must be recognized that such degradation makes lactide polymers desirable as replacements for presently-utilized non-degradable petrochemical-based polymers used for such useful articles as packaging, paper-coating, thin film and other injection-molded or blow-molded articles which are discarded after their useful life.

Applicants have found that the instability of lactide polymers which leads to the beneficial degradation discussed above also creates processing problems. These processing problems include generation of lactide monomer at elevated temperatures and loss in molecular weight believed due to chain scission degradation of the ester bonds and other depolymerization reactions which are not completely understood. Lactide polymer degradation at elevated temperature has been the subject of several studies, including: I. C. McNeill and H. A. Leiper, *Polymer Degradation and Stability*, vol. 11, pp. 267–285 (1985); I. C. McNeill and H. A. Leiper, *Polymer Degradation and Stability*, vol. 11, pp. 309–326 (1985); M. C. Gupta and V. G. Deshmukh, *Colloid & Polymer Science*, vol. 260, pp. 308–311 (1982); M. C. Gupta and V. G. Deshmukh, *Colloid & Polymer Science*, vol. 260, pp. 514–517 (1982); Ingo Luderwald, *Dev. Polymer Degradation*, vol. 2, pp. 77–98 (1979); Domenico Garozzo, Mario Giuffrida, and Giorgio Montaudo, *Macromolecules*, vol. 19, pp. 1643–1649 (1986); and, K. Jamshidi, S. H. Hyon and Y. Ikada, *Polymer*, vol. 29, pp. 2229–2234 (1988), which are incorporated herein by reference. No consensus has been reached as to what are the primary degradation pathways at elevated processing temperatures. As previously disclosed, these may include such pathways as equilibrium-driven depolymerization of lactide polymers to form lactide and chain scission through hydrolysis of the ester bonds along with other pathways. For purposes of the present invention, the exact mechanism of degradation at elevated temperatures is not critical.

It is to be understood, however, that degradation of lactide polymers is both beneficial and detrimental. Benefits derive from degradability when articles manufactured from such polymers are discarded. The same or similar types of degradation are detrimental if they occur during processing or prior to the end of the article's useful life.

Melt-Processing

As disclosed by Gruber et al., a lactide polymer may be extruded, blow-molded, injection-molded, fiber-spun to a non-woven article or processed by any other known melt-processing technique. In most instances, it is recognized that a manufacturer of lactide polymers from a lactide monomer will produce a lactide polymer resin which is in the form of beads or pellets which are sold to a melt-processor. The melt-processor will convert the resin to a useful article utilizing melt-processing encompassing any method of converting a bead or pellet-type resin to a useful article by elevating the temperature of the resin above at least its glass transition temperature but normally higher. Common melt-processing techniques include extrusion, blow-molding, injection-molding, fiber-spinning, film-blowing, film-casting and the like. It is to be understood that the conditions of elevated temperature used in melt-processing cause degradation of lactide polymers during processing. Degradation under melt-processing conditions is shown experimentally in Example 1 based on equilibrium, Example 4 based on catalyst concentration, Example 5 based on catalyst activity, Example 7 based on use of stabilizers and Example 8 based on moisture content. As can be seen in these examples, it is understood that several factors appear to affect the rate of degradation during melt-processing. Applicants have addressed these factors in a combination of compositional requirements and addition of stabilizing or catalyst-deactivating agents to result in a polymer of lactide which is melt-stable.

Melt Stability

The lactide polymers of the present invention are melt-stable. By "melt-stable" it is meant generally that the lactide polymer, when subjected to melt-processing techniques, adequately maintains its physical properties and does not generate by-products in sufficient quantity to foul or coat processing equipment. The melt-stable lactide polymer exhibits reduced degradation relative to known lactide polymers. It is to be understood that degradation will occur during melt-processing. The compositional requirements and use of stabilizing agents as disclosed herein reduces the degree of such degradation to a point where physical properties are not significantly affected by melt-processing and fouling by impurities or degradation by-products does not occur. Furthermore, the melt-stable polymer must be melt-processable in melt-processing equipment such as that available commercially. Further, the polymer must retain molecular weight and viscosity. The polymer must have sufficiently low viscosity at the temperature of melt-processing so that the melt-processing equipment may mechanically, for example, extrude the lactide polymer to a useful article. The temperature at which this viscosity is sufficiently low must also be below a temperature at which substantial degradation occurs.

As detailed in Example 12, a standard test for determining whether a lactide polymer is melt-stable includes placing a small portion of a devolatilized sample of lactide polymer in a closed vial and placing such vial in a 180° C. oil bath. A sample is taken at times of 15 minutes and 1 hour. The melt-stable lactide polymer will show less than 2 percent lactide in the 15-minute sample and, more preferably, less than 2 percent in the 1-hour sample. It is more preferable that the stabilized lactide polymer maintain lactide contents of less than 1 percent in both the 15-minute and 1-hour samples. This comparison is relative to an equilibrium concentration of 3.6 weight percent lactide at 180° C.

Polymer Composition

The melt-stable lactide polymer composition of the present invention comprises a plurality of polylactide polymer chains having a number average molecular weight from about 10,000 to about 300,000. In a preferred composition, the number average molecular weight ranges from about 15,000 to about 150,000. As detailed in Example 3, it appears that the physical properties such as modulus, tensile strength, percentage elongation at break, impact strength, flexural modulus, and flexural strength remain statistically constant when the lactide polymer samples are above a threshold molecular weight. The lower limit of molecular weight of the polymer compositions of the present invention is set at a point above the threshold in order to result in a lactide polymer with predictable physical properties upon melt-processing. As detailed in Example 16, there is a practical upper limit on molecular weight based on increased viscosity with increased molecular weight. In order to melt-process a high molecular weight lactide polymer, the melt-processing temperature must be increased to reduce the viscosity of the polymer. As pointed out in the Example, the exact upper limit on molecular weight must be determined for each melt-processing application in that required viscosities vary and residence time within the melt-processing equipment will also vary. Thus, the degree of degradation in each type of processing system will also vary. Based on the disclosure of Example 16, it is believed that one could determine the suitable molecular weight upper limit for meeting the viscosity and degradation requirements in any application.

The melt-stable lactide polymer compositions in a preferred embodiment are the reaction product of polymerizing a lactide mixture comprising about 5 percent by weight to about 50 percent by weight meso-lactide and about 95 percent by weight or less L-lactide. The optical composition disclosed includes the benefit of utilizing meso-lactide as disclosed by Gruber et al. Further, with this preferred optical composition, the resulting melt-stable lactide polymer is essentially amorphous. In preferred compositions of the present invention, the melt-stable lactide polymer is essentially non-crystalline or essentially amorphous. As detailed in Example 9, amorphous lactide polymers exhibit superior degradability when subjected to a compost test as detailed in the Example or when subjected to chemical hydrolysis as detailed in the Example.

Applicants recognize that an essentially amorphous lactide polymer may have some crystallinity. Crystalline poly L-lactide exhibits an endotherm of roughly 92 Joules per gram at its melting temperature of 170°–180° C. The melting point changes with composition. The degree of crystallinity is roughly proportional to the endotherm on melting. For purposes of the present invention, in preferred embodiments, it is meant by an essentially amorphous or non-crystalline polylactide to be a polylactide or lactide polymer which either exhibits no melting endotherm in the temperature range of 130°–200° C. or which has an energy uptake of less than 10 Joules per gram if an endotherm is present.

The residual monomer concentration in the melt-stable lactide polymer composition is less than 2 percent by weight. In a preferred composition the concentration of lactide in the polymer is less than 1 percent by weight and more preferably less than 0.5 percent by weight. Contrary to disclosures in the art, Applicants have found that the monomer cannot be used as a plasticizing agent in the resin of the present invention due to significant fouling or plating out problems in processing equipment. As detailed in Example 10, it is believed the low levels of monomer concentration do not plasticize the final polymer.

The water concentration within the melt-stable lactide polymer composition is less than about 1,000 parts-per-million. Preferably this concentration is less than 500 parts-per-million and more preferably less than 200 parts-per-million. As detailed in Example 8, the polymer melt-stability is significantly affected by moisture content. Thus, the melt-stable polymer of the present invention must have the water removed prior to melt-processing. Applicants recognize that water concentration may be reduced prior to processing the polymerized lactide to a resin. Thus, moisture control could be accomplished by packaging such resins in a way which prevents moisture from contacting the already-dry resin. Alternatively, the moisture content may be reduced at the melt-processor's facility just prior to the melt-processing step in a dryer. Example 8 details the benefit of drying just prior to melt-processing. Example 11 details the problems encountered due to water uptake in a polymer resin if not stored in a manner in which moisture exposure is prevented-or dried prior to melt-processing. As detailed in these examples, Applicants have found that the presence of water causes excessive loss of molecular weight and generation of decomposition by-products which may affect the physical properties of the melt-processed polymer.

In a preferred composition of the present invention, a stabilizing agent in an amount sufficient to reduce depolymerization of the polylactide polymer during melt-processing to less than 2 percent by weight generation of lactide from a devolatilized sample in the first hour at 180° C. and atmospheric pressure is included in the melt-stable polymer composition. More preferably, the amount of lactide generated is less than 1 percent by weight in the first hour and most preferably less than 0.5 percent by weight in the first hour. The stabilizing agents recognized as useful in the present polymer compositions may include antioxidants and/or water scavengers. Preferable antioxidants are phosphite-containing compounds, hindered phenolic compounds or other phenolic compounds. Antioxidants include such compounds as trialkyl phosphites, mixed alkyl/aryl phosphites, alkylated aryl phosphites, sterically hindered aryl phosphites, aliphatic spirocyclic phosphites, sterically hindered phenyl spirocyclics, sterically hindered bisphosphonites, hydroxyphenyl propionates, hydroxy benzyls, alkylidene bisphenols, alkyl phenols, aromatic amines, thioethers, hindered amines, hydroquinones and mixtures thereof. As detailed in Example 7, many commercially-available stabilizing agents have been tested and fall within the scope of the present melt-stable lactide polymer composition.

The water scavengers which may be utilized in preferred embodiments of the melt-stable lactide polymer composition include: carbodiimides, anhydrides, acyl chlorides, isocyanates, alkoxy silanes, and desiccant materials such as clay, alumina, silica gel, zeolites, calcium chloride, calcium carbonate, sodium sulfate, bicarbonates or any other compound which ties up water. Preferably the water scavenger is degradable or compostable. Example 13 details the benefits of utilizing a water scavenger.

In the manufacture of the melt-stable lactide polymer compositions of the present invention, the reaction to polymerize lactide is catalyzed. Many catalysts have been cited in literature for use in the ring-opening polymerization of lactones. These include but are not limited to: $SnCl_2$, $SnBr_2$, $SnCl_4$, $SnBr_4$, aluminum alkoxides, tin alkoxides, zinc alkoxides, SnO, PbO, Sn (2-ethyl hexanoates), Sb (2-ethyl hexanoates), Bi (2-ethyl hexanoates), Na (2-ethyl hexanoates) (sometimes called octoates), Ca stearates, Mg stearates, Zn stearates, and tetraphenyltin. Applicants have also tested several catalysts for polymerization of lactide at 180° C. which include: tin(II) bis(2-ethyl hexanoate) [T-9, Atochem], dibutyltin diacetate [Fascat 4200®, Atochem], butyltin tris(2-ethyl hexanoate) [Fascat 9102®, Atochem], hydrated monobutyltin oxide [Fascat 9100®, Atochem], antimony triacetate [S-21, Atochem], and antimony tris (ethylene glycoxide) [S-24, Atochem]. Of these catalysts, tin(II) bis(2-ethyl hexanoate), butyltin tris(2-ethyl hexanoate) and dibutyltin diacetate appear to be most effective.

Applicants have found the use of catalysts to polymerize lactide significantly affects the stability of the resin product. It appears the catalyst as incorporated into the polymer also is effective at catalyzing the reverse depolymerization reaction. Example 4 details the effect of residual catalyst on degradation. To minimize this negative effect, in a preferred composition, the residual catalyst level in the resin is present in a molar ratio of monomer-to-catalyst greater than 3,000:1, preferably greater than 5,000:1 and most preferably greater than 10,000:1. Applicants believe a ratio of 20,000:1 may be used, but polymerization will be slow. Optimization of catalyst levels and the benefits associated therewith are detailed in Example 14. Applicants have found that when catalyst level is controlled within these parameters, catalytic activity is sufficient to polymerize the lactide while sufficiently low to enable melt-processing without adverse effect when coupled with low residual monomer level and low water concentration as described above in polymers of molecular weight between 10,000 to about 300,000. It is believed in most applications the addition of a stabilizing agent may be unnecessary if catalyst level is optimized.

Applicants have also found that catalyst concentration may be reduced subsequent to polymerization by precipitation from a solvent. Example 15 demonstrates potential catalyst removal by precipitation from a solvent. This produces a resin with reduced catalyst concentration. In an alternative embodiment, the catalyst means for catalyzing the polymerization of lactide to form the polylactide polymer chains which was incorporated into the melt-stable lactide polymer composition during polymerization is deactivated by including in the melt-stable lactide polymer composition a catalyst deactivating agent in amounts sufficient to reduce catalytic depolymerization of the polylactide polymer chains. Example 5 details the benefits of utilizing a catalyst deactivating agent. Such catalyst-deactivating agents include hindered, alkyl, aryl and phenolic hydrazides, amides of aliphatic and aromatic mono- and dicarboxylic acids, cyclic amides, hydrazones and bishydrazones of aliphatic and aromatic aldehydes, hydrazides of aliphatic and aromatic mono- and dicarboxylic acids, bis-acylated hydrazine derivatives, and heterocyclic compounds. A preferred metal deactivator is Irganox® MD1024 from Ciba-Geigy.

In an alternative embodiment, the catalyst concentration is reduced to near zero by utilizing a solid-supported catalyst to polymerize lactide. The feasibility of utilizing such catalyst is detailed in Example 2. It is believed catalysts which may be utilized include supported metal catalysts, solid acid catalysts, acid clays, alumina silicates, alumina, silica and mixtures thereof.

A preferred melt-stable lactide polymer composition is the reaction product of polymerization of lactide at a temperature greater than about 160° C. Applicants have found that polymerization at higher temperatures result in a characteristically different polymer which is believed to have higher melt stability due to increased transesterification during polymerization. The benefits of higher temperature polymerization are detailed in Example 6.

Melt-Stable Lactide Polymer Process

The process for the manufacture of a melt-stable lactide polymer comprises the steps of first providing a lactide mixture wherein the mixture contains about 5 percent by weight to about 50 percent by weight meso-lactide and about 95 percent by weight or less L-lactide. Such purified lactide stream may be such as that produced in the process disclosed by Gruber et al., although the source of lactide is not critical to the process of the present invention.

The lactide mixture is polymerized to form a lactide polymer or polylactide with some residual unreacted monomer in the presence of a catalyst means for catalyzing the polymerization of lactide to form polylactide. Catalysts suitable for such polymerization have been listed previously. The concentration of catalysts utilized may be optimized as detailed in the following examples and discussed previously.

In a preferred embodiment, a stabilizing agent as disclosed above, which may be an antioxidant and/or a water scavenger is added to the lactide polymer. It is recognized that such stabilizing agents may be added simultaneously with or prior to the polymerization of the lactide to form the lactide polymer. The stabilizing agent may also be added subsequent to polymerization.

As previously disclosed, the stabilizing agent is added in a sufficient amount to reduce depolymerization of polylactide during melt-processing to less than 2 percent by weight generation of lactide from a devolatilized sample in the first hour at 180° C. and atmospheric pressure. More preferably, the stabilizing agent controls lactide generation to less than 1 percent by weight and most preferably less than 0.5 percent by weight in the first hour at 180° C. and atmospheric pressure. Alternatively, the control of catalyst concentration to optimize the balance between necessary catalytic activity to produce polylactide versus the detrimental effects of catalytic depolymerization or degradation of the lactide polymer may be utilized to prevent the need for adding a stabilizing agent.

The lactide polymer is then devolatilized to remove unreacted monomer which may also be a by-product of decomposition reactions or the equilibrium-driven depolymerization of polylactide. Any residual water which may be present in the polymer would also be removed during devolatilization, although it is recognized that a separate drying step may be utilized to reduce the water concentration to less than about 1,000 parts-per-million. The devolatilization of the lactide polymer may take place in any known devolatilization process. The key to selection of a process is operation at an elevated temperature and usually under conditions of vacuum to allow separation of the volatile components from the polymer. Such processes include a stirred tank devolatilization or a melt-extrusion process which includes a devolatilization chamber and the like.

In a preferred process for manufacture of a melt-stable lactide polymer composition, the process also includes the step of adding a molecular weight control agent to the lactide prior to catalyzing the polymerization of the lactide. Molecular weight control agents include active hydrogen-bearing compounds, such as lactic acid, esters of lactic acid, alcohols, amines, glycols, diols and triols which function as chain-initiating agents. Such molecular weight control agents are added in sufficient quantity to control the number average molecular weight of the polylactide to between about 10,000 and about 200,000.

Next referring to FIG. 1 which illustrates a preferred process for producing a melt-stable lactide polymer composition. A mixture of lactides enters a mixing vessel (3) through a pipeline (1). A catalyst for polymerizing lactide is also added through a pipeline (13). Within mixing vessel (3) a stabilizing agent may be added through a pipeline (2). A water scavenger may also be added through the pipeline (2). The stabilized lactide mixture is fed through a pipeline (4) to a polymerization process (5). The polymerized lactide or lactide polymer leaves the polymerization process through a pipeline (6). The stream is fed to a second mixing vessel (8) within which a stabilizing agent and/or catalyst deactivating agent may be added through a pipeline (7). The stabilized lactide polymer composition is then fed to a devolatilization process (10) through a pipeline (9). Volatile components leave the devolatilization process through a pipeline (11) and the devolatilized lactide polymer composition leaves the devolatilization process (10) in a pipeline (12). The devolatilized lactide composition is fed to a resin-finishing process (14). Within the resin-finishing process the polymer is solidified and processed to form a pelletized or granular resin or bead. Applicants recognize the polymer may be solidified and processed to form resin or bead first, followed by devolatilization. The resin is then fed to a drying process (16) by conveyance means (15). Within the drying process (16) moisture is removed as a vapor through pipeline (17). The dried lactide polymer resin leaves the drying process (16) by a conveyance means (18) and is fed to a melt-processing apparatus (19). Within the melt-processing apparatus (19) the resin is converted to a useful article as disclosed above. The useful article leaves the melt-processing apparatus (19) through a conveyance means (20).

EXPERIMENTAL

The following examples further detail advantages of the system disclosed herein:

Example 1

Lactide and Polylactide Equilibrium Concentrations

Experiments were conducted to determine the equilibrium concentration of lactide and polylactide at different temperatures. In these experiments a sample of lactide was polymerized in the presence of a catalyst (tin (II) bis(2-ethyl hexanoate) and held at a fixed temperature for 18 hours or greater. Beyond this time the residual monomer concentration is believed essentially constant. The content of residual monomer was determined by GPC analysis. GPC analysis was conducted with an Ultrastyragel® column from waters Chromatography. The mobile phase was chloroform. A refractive index detector with molecular weight calibration using polystyrene standards was used. The GPC temperature was 35° C. Data analysis was completed using the software package Baseline, model 810, version 3.31.

Figure 2:
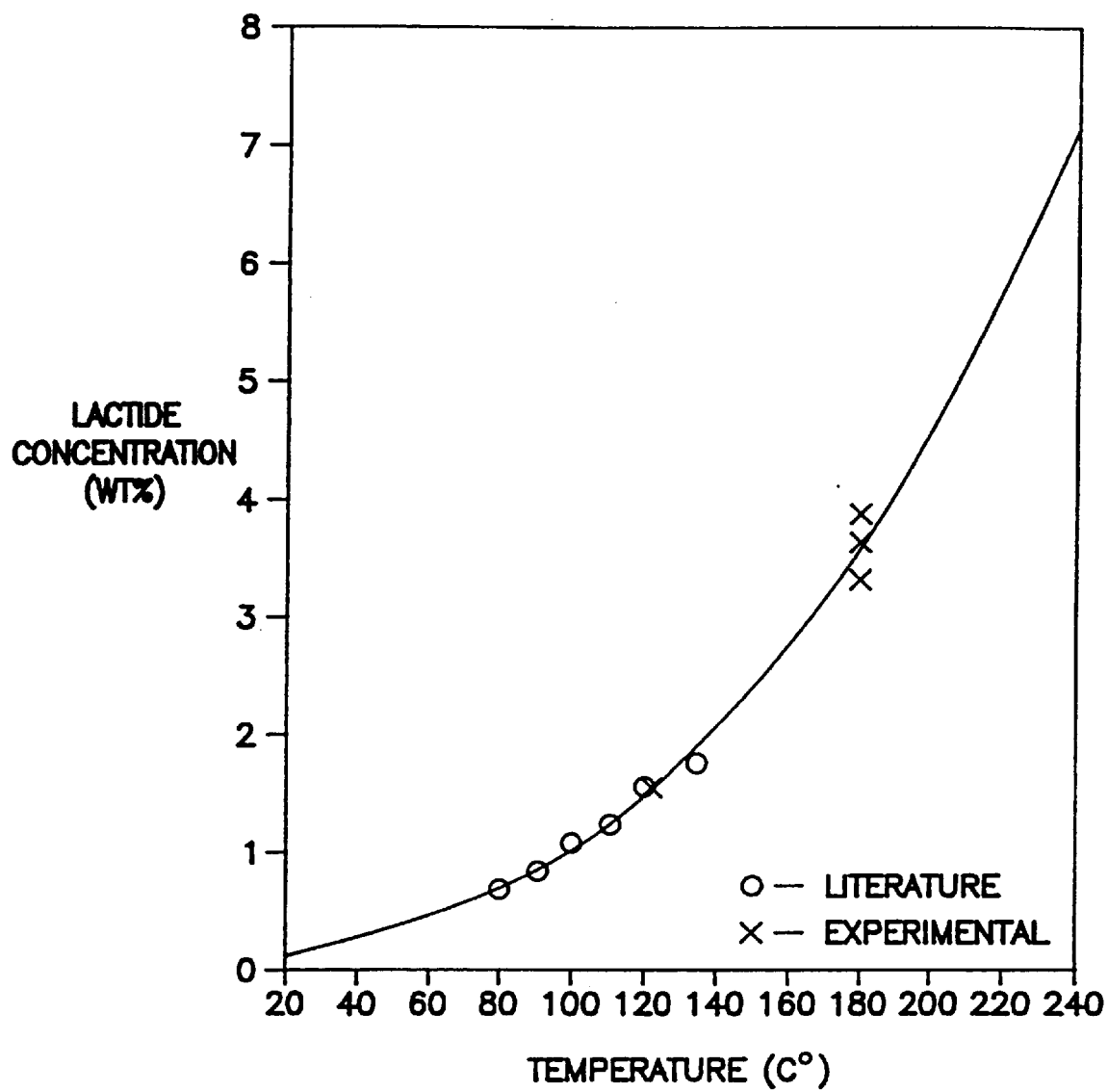
FIG. 2 is a graph showing the equilibrium relationship between lactide and polylactide at various temperatures.

The results of tests conducted on several samples at various temperatures are summarized in the graph of FIG. 2 as indicated by X's on such graph. Also plotted on the graph of FIG. 2 are data points cited in A. Duda and S. Penczek, *Macromolecules,* vol. 23, pp. 1636–1639 (1990) as indicated by circles on the graph. As can be seen from the graph of FIG. 2, the equilibrium concentration, and thus the driving force behind the depolymerization of polylactide to form lactide, increases dramatically with increased temperature. Thus, melt-processing at elevated temperatures results in degradation of the lactide polymer to form lactide on the basis of equilibrium alone. For example, lactide concentrations below about 2 percent cannot be directly obtained at temperatures of 140° C. or above due to the identified equilibrium relationship between lactide and polylactide.

Example 2

Lactide Polymerization in the Presence of a Solid Supported Catalyst

Tin (II) Oxide 24 grams of L-lactide and 6 grams of D,L-lactide were combined in a round bottom flask with 0.033 grams of Tin (II) oxide, as a fine powder. This corresponds to the catalyst level of 852:1, molar ratio lactide to tin. The flask was then purged with dry nitrogen 5 times. This was lowered into an oil bath at 160° C. with magnetic stirring. Polymerization time was 8 hours.

Amberlyst 36

24 grams of L-lactide and 6 grams of D,L-lactide were combined in a round bottom flask with 1.06 grams of Amberlyst 36 resin beads. The flask was purged 5 times with dry nitrogen. The flask was lowered into an oil bath at 140° C. with magnetic stirring. Polymerization time was 8 hours. The resin was a stated proton content of 1 Meq/gram dry weight resin. The resin was prepared by rinsing 2 times with 10 volumes dry methanol, then dried for several hours under high vacuum for several hours at 40° C.

The polymerization results are shown below:

TABLE 1

| Sample | Mn | Mw | PDI | % Conversion |
| --- | --- | --- | --- | --- |
| Tin (II) Oxide | 77,228 | 103,161 | 1.34 | 54.0 |
| Amberlyst | 1,112 | 1,498 | 1.34 | 73.5 |

Example 3

Molecular Weight Relationship to Physical Properties of Lactide Polymers

Polylactide samples with various molecular weights and optical compositions were prepared by polymerizing blends of L-lactide and meso-lactide at 180° C. under nitrogen in a 1-gallon sealed reactor. Tin(II) bis(2-ethyl hexanoate) catalyst was added at a monomer-to-catalyst ratio of 10,000:1. After about 1 hour the molten polymer was drained from the reactor using nitrogen pressure. The sample was poured into a pan and placed in a vacuum oven at about 160° C. for about 4 hours to bring the reaction to near equilibrium levels.

The samples were ground and analyzed by GPC (the method of Example 1) to determine the initial molecular weight. Portions of the samples were then dried under vacuum and processed in an injection molding apparatus (New Britian 75 from New Britian Machine Co.) to produce standard test bars for physical property testing. The results of physical property testing are shown in Table 2 on the following page. The physical property tests were made according to ASTM methods D 638, D 256, and D 790. The reported results are the averages of several tests.

Samples of the test bars after injection molding were again analyzed by GPC for molecular weight as a measure of the effect of one type of melt-processing on polymer degradation. Other portions of the test bars were reground and tested in a capillary viscometer to determine the melt-viscosity. These results are also included in Table 2.

Statistical analysis of the data revealed no correlations which were statistically significant between either optical composition or molecular weight and the mechanical properties of modulus, tensile strength, percentage elongation at break, notched Izod impact strength, flexural modulus, or flexural strength. The independence of these properties on molecular weight indicates that all of these samples were above a "threshold" molecular weight required to achieve the intrinsic properties of the polymer in a preferred composition.

The viscosity data show significant correlations with molecular weight. This dependence documents the practical limitation and necessity of controlling polymer molecular weight below an upper limit at which it is impractical to melt-process the polymer. At high molecular weight, high viscosity prevents processing by standard melt-processing equipment. Increases in temperature to reduce viscosity dramatically increase polymer degradation which is also unacceptable.

weight. The GPC apparatus for this test was a Viscotek Model 200 GPC and a Phenomenex column. The TGA analysis typically resulted in about a 5% loss in weight and molecular weight drops of 0 to 70%.

The number average molecular weights were converted to a milliequivalent per kilogram basis (1,000,000/Mn) in order to calculate a rate of-chain scission events. The results below represent averages of 2–4 replicates on each of the four samples.

TABLE 3

| Catalyst level (monomer/catalyst) | Scission Rate (meq/kg*min) |
|---|---|
| 5,000 | 1.33 |
| 10,000 | 0.62 |
| 20,000 | 0.44 |
| 40,000 | 0.12 |

The rate of chain scission was directly proportional to the residual catalyst level, demonstrating the detrimental effect of catalyst activity on melt-stability under conditions similar to melt-processing. This instability, however, is distinguished from the instability due to the equilibrium relationship between lactide and polylactide detailed in Example 1, in that loss of molecular weight due to catalytic depolymerization by chain scission is evident.

TABLE 2

| Sample I.D. | Meso Lactide In Blend, Wt % | Initial Molecular Weight | Molecular Weight After Injection Molding | Initial IV (dl/g) | Final IV (dl/g) | Viscosity at 173° C. (Pa · S) Shear Rate 100 S$^{-1}$ | Viscosity at 173° C. (Pa · S) Shear Rate 1000 S$^{-1}$ |
|---|---|---|---|---|---|---|---|
| 6 | 40 | 59000 | 41000 | 0.77 | 0.86 | 5.5 | 2.9 |
| 5 | 10 | 81000 | 54000 | 0.85 | 0.88 | 10.4 | 7.2 |
| 4 | 20 | 69000 | 59000 | 1.05 | 0.91 | 10.4 | 7.2 |
| 8 | 10 | 146000 | 64000 | 1.76 | 1.02 | 15.7 | 10.0 |
| 9 | 40 | 83000 | 68000 | 1.11 | 0.97 | 12.6 | 8.1 |
| 7 | 20 | 116000 | 71000 | 1.57 | 1.16 | 36.0 | 12.9 |
| 10 | 20 | 146000 | 83000 | 1.65 | 1.19 | 35.8 | 15.8 |

Mechanical Properties of Injection Molded Samples

| Sample I.D. | Modulus MPSI | Tensile Strength (Yld) PSI | % Elongation at Break | IZOD Impact ft · lb./in | Flexural Modulus MPSI | Flexural Strength PSI |
|---|---|---|---|---|---|---|
| 6 | 0.55 | 6600 | 3.3 | 0.39 | 0.53 | 11300 |
| 5 | 0.56 | 7800 | 3.5 | 0.46 | 0.54 | 12500 |
| 4 | 0.56 | 7600 | 3.9 | 0.32 | 0.53 | 12500 |
| 8 | 0.55 | 7700 | 3.4 | 0.47 | 0.53 | 12400 |
| 9 | 0.59 | 6700 | 3.1 | 0.42 | 0.52 | 10600 |
| 7 | 0.56 | 7400 | 3.3 | 0.45 | 0.51 | 12400 |
| 10 | 0.55 | 6700 | 3.0 | 0.47 | 0.52 | 9900 |

Example 4

Effect of Residual Catalyst on Polymer Degradation

Polymer samples were prepared at four levels of catalyst, corresponding to monomer to catalyst molar ratios of 5,000:1, 10,000:1, 20,000:1, and 40,000:1. The catalyst utilized was tin (II) bis(2-ethyl hexanoate). These samples were then subjected to heating in a TGA apparatus (TA Instruments, Inc., model 951 thermogravimetric analyzer with a DuPont 9900 computer support system) with a nitrogen purge. Isothermal conditions of 200° C. for 20 minutes were used. The samples were then analyzed by GPC with a viscosity-based detector and a universal calibration curve to determine the extent of breakdown in molecular Example 5

Catalyst Deactivation Experiment

Two runs were made in a laboratory Parr reactor. Lactide feed was 80% L-lactide and 20% D,L-lactide. Molecular weight was controlled by adding a small quantity of lactic acid, the target molecular weight was 80,000 Mn.

Lactide was charged to the reactor as a dry mix, the reactor was purged 5 times with nitrogen, and heated up to 180° C. At this point catalyst (5000:1 monomer to catalyst molar ratio, Fascat 2003) was charged through a port in the top of the reactor. The reaction was allowed to proceed for 70 minutes at 180° C., with mechanical agitation. Conversion at this point was 93–94%, close to the equilibrium value at 180° C. of 96% polylactide from FIG. 2. This point is considered t-zero, designating the completion of the polymerization reaction and the beginning of the mixing time.

In the control experiment, a sample was taken and the mixture was held at temperature with continued agitation. Samples were taken periodically through a port in the reactor bottom. After 4 hours the reactor was drained.

In the example experiment, a sample was taken and 0.25 weight % of a metal deactivator (Irganox® MD 1024®) was added through the catalyst addition port. The mixture was held at temperature with continued agitation and samples were withdrawn periodically. The reactor was drained after 4 hours.

GPC analysis (utilizing the method of Example 1) for these samples was divided into three parts: polymer with molecular weight over 4,000 (for which the Mn and Mw numbers are reported), the % oligomers (comprising the region with molecular weight greater than lactide but less than 4,000, as distinguished from oligomers as defined by Loomis to include only oligomers up to a molecular weight of 450), and % lactide (residual monomer). The structure of the oligomers was not certain, but it is believed they were primarily cyclic structures. It is also believed that the metal deactivator, if unreacted, will elute with the oligomer fraction. Quantification of the oligomer fraction is difficult, because the GPC trace is near the baseline in this region.

The analysis of the polymer samples as withdrawn from the reactor at various time intervals for the control and experimental compositions are shown below in Table 4.

TABLE 4

|  | Mn | Mw | % Polymer | % Oligomer | % Monomer |
| --- | --- | --- | --- | --- | --- |
| Control |  |  |  |  |  |
| t-zero | 67,100 | 119,500 | 94 | 0 | 6.0 |
| 0.5 hr | 62,500 | 119,000 | 95 | 0.7 | 3.9 |
| 1.0 hr | 61,500 | 116,100 | 96 | 0 | 3.6 |
| 1.5 hr | 56,000 | 111,600 | 95 | 1.5 | 3.3 |
| 2.0 hr | 57,600 | 110,900 | 96 | 0.9 | 3.1 |
| 4.0 hr | 51,400 | 105,400 | 94 | 3.3 | 3.1 |
| Test |  |  |  |  |  |
| t-zero | 63,200 | 110,700 | 93 | 3.5 | 3.8 |
| 0.5 hr | 52,100 | 108,600 | 92 | 4.6 | 2.9 |
| 1.0 hr | 52,700 | 109,200 | 92 | 4.9 | 2.8 |
| 1.5 hr | 53,400 | 107,200 | 93 | 4.0 | 3.1 |
| 2.0 hr | 59,700 | 111,100 | 94 | 0.6 | 5.8 |
| 4.0 hr | 51,200 | 107,300 | 91 | 6.1 | 3.3 |

The samples were then ground and placed in a 120° C. oven under vacuum (pressure 0.1 inch Hg) for 14 hours. Sample analyses after this treatment are shown below in Table 5.

TABLE 5

|  | Mn | Mw | % Polymer | % Oligomer | % Monomer |
| --- | --- | --- | --- | --- | --- |
| Control |  |  |  |  |  |
| t-zero | 45,500 | 88,500 | 98 | 2.2 | 0.0 |
| 0.5 hr | 45,000 | 88,700 | 98 | 2.0 | 0.0 |
| 1.0 hr | 43,900 | 87,200 | 98 | 2.0 | 0.0 |
| 1.5 hr | 42,600 | 84,000 | 98 | 2.2 | 0.0 |
| 2.0 hr | 42,000 | 85,200 | 97 | 3.2 | 0.0 |
| 4.0 hr | 41,900 | 82,800 | 98 | 2.0 | 0.0 |
| Test |  |  |  |  |  |
| t-zero | 39,300 | 76,700 | 96 | 4.0 | 0.0 |

TABLE 5-continued

|  | Mn | Mw | % Polymer | % Oligomer | % Monomer |
| --- | --- | --- | --- | --- | --- |
| 0.5 hr | 43,900 | 85,100 | 98 | 2.4 | 0.0 |
| 1.0 hr | 55,300 | 98,600 | 96 | 3.8 | 0.0 |
| 1.5 hr | 48,400 | 96,200 | 95 | 4.5 | 0.0 |
| 2.0 hr | 48,900 | 101,900 | 95 | 5.0 | 0.0 |
| 4.0 | 50,600 | 101,900 | 94 | 5.6 | 0.0 |

In all cases the polymer was completely devolatilized (0.0% residual lactide monomer). The data also clearly show that the metal deactivator reduced the degradation of polymer during the devolatilization step (as indicated by the greater loss in Mn for the control samples from Table 4 to Table 5 versus the Test samples). One hour of mixing appears to be long enough to develop most of the benefit.

The samples were stored at room temperature under nitrogen for about 1 week and reanalyzed, as shown below in Table 6.

TABLE 6

|  | Mn | Mw | % Polymer | % Oligomer | % Monomer |
| --- | --- | --- | --- | --- | --- |
| Control |  |  |  |  |  |
| t-zero | 33,500 | 71,000 | 100 | 0.1 | 0.0 |
| 0.5 hr | 43,400 | 95,800 | 99 | 1.0 | 0.0 |
| 1.0 hr | 44,900 | 96,300 | 100 | 0.1 | 0.0 |
| 1.5 hr | 45,900 | 95,000 | 100 | 0.0 | 0.0 |
| 2.0 hr | 45,900 | 94,100 | 100 | 0.2 | 0.0 |
| 4.0 hr | 43,100 | 90,100 | 99 | 1.3 | 0.0 |
| Test |  |  |  |  |  |
| t-zero | 44,600 | 84,900 | 100 | 0.0 | 0.0 |
| 0.5 hr | 45,300 | 90,600 | 99 | 1.2 | 0.0 |
| 1.0 hr | 47,800 | 100,000 | 98 | 2.4 | 0.0 |
| 1.5 hr | 46,600 | 98,900 | 96 | 3.5 | 0.0 |
| 4.0 | 57,700 | 110,200 | 96 | 4.0 | 0.3 |

Equilibrium lactide levels are estimated to be less than 0.2 weight % at room temperature. Consistent with that, essentially no lactide was observed in any of the samples (detection limit about 0.1 wt %). The oligomer content in the non-stabilized samples declined and some increase in molecular weight was noted, perhaps due to reincorporation of the (cyclic) oligomers into the polymer. The oligomer depletion reaction was inhibited in the stabilized polymers, with the extent of inhibition dependent on the length of time that the additive was mixed.

The samples were then reheated to 180° C. in sealed vials and held for one hour as a simulation of melt-processing. Analysis of the samples after the heat treatment is given below in Table 7.

TABLE 7

|  | Mn | Mw | % Polymer | % Oligomer | % Monomer |
| --- | --- | --- | --- | --- | --- |
| Control |  |  |  |  |  |
| t-zero | 23,900 | 60,000 | 88 | 8.4 | 4.0 |
| 0.5 hr | 23,900 | 59,600 | 90 | 7.7 | 2.7 |
| 1.0 hr | 23,700 | 58,800 | 88 | 9.3 | 2.7 |
| 1.5 hr | 24,700 | 58,000 | 86 | 10.0 | 3.8 |
| 2.0 hr | 26,100 | 56,400 | 90 | 6.8 | 2.7 |
| 4.0 hr | 24,800 | 58,700 | 92 | 6.6 | 1.9 |
| Test |  |  |  |  |  |
| t-zero | 33,900 | 64,300 | 95 | 2.2 | 3.1 |

TABLE 7-continued

|  | Mn | Mw | % Polymer | % Oligomer | % Monomer |
|---|---|---|---|---|---|
| 0.5 hr | 17,900 | 34,600 | 94 | 4.8 | 1.7 |
| 1.0 hr | 21.200 | 42,900 | 94 | 4.6 | 1.8 |
| 1.5 hr | 29,200 | 56,900 | 98 | 0.5 | 1.8 |
| 2.0 hr | missing | | | | |
| 4.0 hr | 35,700 | 71,400 | 95 | 3.7 | 1.7 |

The data for molecular weight show that if the metal deactivator is not mixed into the system long enough then it can have a detrimental impact on stability in the melt. The samples for which the mixing was at least 1.5 hours show no detrimental effect, and the 4 hour sample appears to be somewhat more stable than any of the others based on molecular weight alone. More importantly, the metal deactivator samples show significantly less lactide reformation than the control samples. This effect is gained even in the samples which were mixed for only 0.5 hour. The metals deactivated samples averaged over 1.8% lactide after one hour at 180° C., compared to an average of 3.0% lactide for the controls. The equilibrium level at 180° C. is about 3.6% from FIG. 2. Thus, the use of metal deactivators can reduce the troublesome reformation of lactide during melt-processing of the finished polymer.

Example 6

Effect of Increased Polymerization Temperature on Polymer Characteristics

L-lactide (Boeringer Ingleheim, S-grade) was used as received, meso-lactide (PURAC) was purified by redistillation to remove traces of D- and L-lactide. The melting point of the purified meso-lactide was 54° C. Lactide mixtures were made up to the following ratios: 100% L-lactide, 90/10 L-lactide/meso-lactide, 70/30 L-lactide/meso-lactide, 50/50 L-lactide/meso-lactide, and 100% meso-lactide. Catalyst level was 2,500:1 molar ratio of monomer to tin added as Fascat® 9002. Lactic acid was added as a molecular weight control agent to target a number average molecular weight of 50,000 (the same amount was added to all samples). Polymerization times were estimated to obtain conversions of 50% and 90%. For 120° C. this was 4 hours and 16 hours, respectively. For 180° C. these times were 10 minutes and 50 minutes, respectively. Below in Table 8 are the GPC results (method of Example 1) of tests on the polymer samples produced by this procedure.

TABLE 8

| l/meso | Temp | Mn | Mw | PDI | % Conv |
|---|---|---|---|---|---|
| 100% l | 120° C. | 31,014 | 33,774 | 1.09 | 53.2 |
| | | 45,864 | 52,574 | 1.15 | 87.1 |
| 100% l | 180° C. | 27,785 | 32,432 | 1.17 | 46.7 |
| | | 56,839 | 98,125 | 1.73 | 93.3 |
| 90/10 | 120° C. | 34,541 | 38,586 | 1.12 | 62.3 |
| | | 29,222 | 34,466 | 1.18 | 89.3 |
| 90/10 | 180° C. | 31,632 | 35,713 | 1.13 | 48.5 |
| | | 57,925 | 110,841 | 1.91 | 94.8 |
| 70/30 | 120° C. | 41,211 | 45,222 | 1.10 | 60.1 |
| | | 58,284 | 71,257 | 1.22 | 89.1 |
| 70/30 | 180° C. | 32,292 | 37,401 | 1.16 | 53.8 |
| | | 51,245 | 107,698 | 2.10 | 96.5 |
| 50/50 | 120° C. | 15,888 | 17,969 | 1.13 | 57.8 |
| | | 25,539 | 31,834 | 1.25 | 90.6 |
| 50/50 | 180° C. | 34,375 | 42,018 | 1.22 | 62.5 |
| | | 44,590 | 98,028 | 2.20 | 95.5 |
| 100% meso | 120° C. | 33,571 | 40,635 | 1.21 | 73.4 |
| | | 45,237 | 68,142 | 1.51 | 94.3 |
| 100% meso | 180° C. | 30,976 | 42,987 | 1.39 | 67.6 |
| | | 40,038 | 83,815 | 2.09 | 96.6 |

The results show that the ultimate number average molecular weight was not significantly affected by the temperature of polymerization, with an average of 41,000 at 120° C. and 50,000 at 180° C. This implies that each lactic acid molecule initiates about one polymer chain, regardless of temperature. The ultimate weight average molecular weight is, however, significantly affected by temperature. At 120° C. the weight average molecular weight averaged 52,000 and at 180° C. the average was 100,000. This is believed to be due to a relative increase in the rate of transesterification at 180° C. The polydispersity index (PDI) at high conversion also reflects this, averaging 1.3 at 120° C. and 2.0 at 180° C. It is believed these differences would have a significant effect on the melt-processing characteristics of the polymer, with the higher weight average molecular weight of the polymer produced at 180° C. expected to translate into better melt strength and processability.

These experiments show that polymerization at a higher temperature results in a polymer that is characteristically different, even though the polymers have a similar number average molecular weight, the weight average molecular weight is much higher. This difference is also reflected in the polydispersity index (PDI). High temperature polymerization which gives a higher weight average molecular weight will give a higher melt strength and better processability. This is believed due to increased transesterification rates relative to polymerization rate. Further, the glass transition temperature for the samples polymerized at higher temperature is higher, further evidencing that polymers of the same composition but polymerized at higher temperatures are more melt-stable.

Example 7

Experiments with Stabilizing Agents and Metal Deactivators

Test 1

Conditions: vial polymerization, (Lactide is melted under a nitrogen-purged atmosphere in a round bottom flask with stirring. Catalyst and additives are added and aliquots of the mixtures are pipetted into silanized glass vials. Typically 5–10 grams of reaction mixture are used in a 16 ml. vial. The vials are tightly capped and placed into a preheated oil bath.) 10,000:1 molar ratio of lactide-to-tin, tin(II) bis(2-ethyl hexanoate) catalyst, 0.2 wt % Ultranox® 626 in tetrahydrofuran (THF). 180° C. Time was 90 minutes. Purchased lactide was used.

The control with tin only polymerized to 84% conversion and reached a MWn of 31,700. The example with tin and Ultranox® polymerized to 83% conversion and reached a MWn of 39,800; an increase of 26% over the control.

The control sample turned light yellow, the sample with stabilizer remained colorless.

Test 2

Conditions: vial polymerization, 5000:1 molar ratio of lactide to tin, tin(II) bis(2-ethyl hexanoate) catalyst, 0.25 wt % Ultranox® 626 (in THF). 180° C. Time was 60 minutes. Pilot plant lactide was used.

The control with tin alone polymerized to 67% conversion and reached a MWn of 62,900. The example with tin and Ultranox® polymerized to 66% conversion and reached a MWn of 75800; an increase of 21% over the control.

A second example with tin(II) bis(2-ethyl hexanoate), Ultranox®, and 0.50% of Irganox® 1076, which is a phenolic antioxidant, polymerized to 66% conversion and reached a number average molecular weight (MWn) of 74500; an increase of 18% over the control.

All samples were a dark yellow color, although the samples with stabilizer had a slightly lower absorbance at 300 nm.

Test 3

Conditions: vial polymerization, 10,000:1 molar ratio of lactide to tin, tin(II) bis(2-ethyl hexanoate) catalyst, 180° C., 80% L-lactide and 20% D,L-lactide purchased from Henley and Aldrich, respectively. Lactic acid was added to control molecular weight to about 75,000 at full conversion. One sample included 0.25% Ultranox® 626 phosphite stabilizer, one included 0.25% Irganox® 1076 antioxidant, and one control sample.

Samples were taken at various times and analyzed by GPC for conversion and molecular weight (the method of Example 1). The results are summarized in Table 9 below.

TABLE 9

| Time | Control | | Irganox ® | | Ultranox ® | |
|---|---|---|---|---|---|---|
| (hrs) | Mn | % conv | Mn | % conv | Mn | % conv |
| 1 | 31,000 | 46 | 35,900 | 41 | 65,500 | 61 |
| 2 | 45,400 | 74 | 56,800 | 74 | 102,700 | 83 |
| 4 | 69,600 | 93 | 74,100 | 93 | 97,200 | 91 |
| 11 | 52,900 | 95 | 60,700 | 95 | 71,500 | 94 |

The sample with phosphite stabilizer polymerized faster, shown by the higher conversion at 1 and 2 hours, and went to a higher molecular weight than the control or the sample with Irganox. The phosphite stabilized sample had a molecular weight more than 30% higher than the control for all time periods.

Test 4

The experiment above was repeated to compare the control to the phosphite-stabilized polymer, as summarized in Table 10 below.

TABLE 10

| Time | Control | | Ultranox ® | |
|---|---|---|---|---|
| (hrs) | Mn | % conv | Mn | % conv |
| 1 | 36,600 | 37 | 71,500 | 59 |
| 2 | 51,700 | 70 | 95,200 | 85 |
| 4 | 64,400 | 91 | 103,700 | 94 |
| 8 | 58,100 | 96 | 95,700 | 94 |

The sample with phosphite stabilizer again polymerized faster and went to a higher molecular weight than the non-stabilized sample. The phosphite stabilized sample had a molecular weight more than 60% higher than the control for all time periods.

Test 5

Conditions: vial polymerization, 5,000:1 molar ratio of lactide to tin, tin(II) bis(2-ethyl hexanoate) catalyst, 180° C., 80% L-lactide and 20% D,L-lactide purchased from Henley and Aldrich. Lactic acid was added to control number average molecular weight to an estimated 80,000 at full conversion. One sample was run with 0.25% Ultranox® 626 phosphite stabilizer, one with 0.25% Irganox® 1076 antioxidant, and one control sample.

Samples taken at various times and analyzed by GPC (the method of Example 1) for conversion and molecular weight. The results are tabulated in Table 11 below.

TABLE 11

| Time | Control | | Irganox ® | | Ultranox ® | |
|---|---|---|---|---|---|---|
| (hrs) | Mn | % conv | Mn | % conv | Mn | % conv |
| 1 | 83,600 | 76 | 121,900 | 83 | 162,300 | 87 |
| 4 | 74,400 | 93 | 104,300 | 95 | 123,900 | 96 |
| 24 | 40,200 | 96 | 52,000 | 96 | 96,900 | 97 |
| 48 | 34,200 | 97 | 30,400 | 96 | 56,500 | 96 |
| 72 | 23,000 | 96 | 22,400 | 96 | 69,500 | 96 |

The phosphite-stabilized sample had a molecular weight more than 60% higher than the control for all time periods. After 72 hours it had a molecular weight 2.8 times higher than the control. The sample with antioxidant showed an initial increase in molecular weight, relative to the control, but the effect disappeared after 48 hours.

The phosphite stabilized sample was significantly lighter in color than the control or the antioxidant treated sample.

Test 6

Conditions: vial polymerization, 5000:1 molar ratio of lactide to tin, tin(II) bis(2-ethyl hexanoate) catalyst, 0.25 wt % Ultranox® 626 (in THF). 180° C. Time was two hours. Pilot plant lactide washed with isopropyl alcohol was used.

The control with tin alone polymerized to 95% conversion and reached a number average molecular weight of 118,000. The example with tin and Ultranox® polymerized to 93% conversion and reached a number average molecular weight of 151,000, an increase of 28% over the control.

Test 7

Conditions: vial polymerization at 180° C. 5000:1 molar ratio of lactide to tin, tin(II) bis(2-ethyl hexanoate) catalyst. Lactide was 80% L-lactide and 20% D,L-lactide, purchased from Henley and from Aldrich. Lactic acid was added to target the molecular weight to an Mn of 80,000. All stabilizers were added at 0.25 weight percent. Molecular weight (number average) was determined for samples pulled at 3 hours, while rate constants were based on samples pulled at 1 hour. The results of these screening tests on many stabilizing agents following the above procedure are detailed below in Table 12. Product designations in Table 12 are tradenames or registered trademarks.

TABLE 12

| Sample | | Mn | % Conversion | Relative Rate |
|---|---|---|---|---|
| Control 1 | | 65,000 | 95.9 | 90 |
| Control 2 | | 85,000 | 95.9 | 100 |
| Control 3 | | 76,000 | 96.6 | 100 |
| Control 4 | | 69,000 | 96.2 | 100 |
| Control 5 | | 74,000 | 96.8 | 110 |
| Control 6 | | 70,000 | 97.2 | 110 |
| PHOSPHITES | | | | |
| Ultranox 626 | (GE) | 103,000 | 96.8 | 100 |
| Weston TDP | (GE) | 64,000 | 70.0 | 60 |
| Weston PDDP | (GE) | 67,000 | 76.7 | 60 |
| Weston PNPG | (GE) | 92,000 | 94.1 | 100 |

TABLE 12-continued

| Sample | | Mn | % Conversion | Relative Rate |
|---|---|---|---|---|
| Irgafos 168 | (Ciba-Geigy) | 95,000 | 95.3 | 120 |
| Weston 618 | (GE) | 99,000 | 95.1 | 100 |
| Sandostab P-EPQ | (Sandoz) | 108,000 | 94.7 | 110 |
| Weston TNPP | (GE) | 88,000 | 97.9 | 130 |
| PHENOLIC ANTIOXIDANTS | | | | |
| Irganox 1010 | (Ciba-Geigy) | 95,000 | 97.5 | 110 |
| Cyanox 1790 | (Cyanamid) | 98,000 | 96.9 | 120 |
| BHT | | 87,000 | 96.5 | 130 |
| Irganox 1076 | (Ciba-Geigy) | 121,000 | 97.8 | 130 |
| Topanol CA | (ICI) | 84,000 | 96.6 | 160 |
| AMINES | | | | |
| Tinuvin 123 | (Ciba-Geigy) | 65,000 | 94.8 | 70 |
| Tinuvin 622 | (Ciba-Geigy) | 82,000 | 95.7 | 80 |
| Naugard 445 | (Uniroyal) | 93,000 | 98.2 | 120 |
| THIOETHER | | | | |
| Mark 2140 | (Witco) | 77,000 | 97.0 | 120 |
| METAL DEACTIVATORS | | | | |
| Irganox MD1024 | (Ciba-Geigy) | 34,000 | 65.7 | 10 |
| Naugard XL-1 | (Uniroyal) | 91,000 | 95.8 | 110 |

Note, that with a few exceptions, the phosphites and the phenolic antioxidants provide increased molecular weight with no reduction in polymerization rate. Of the amines, only Naugard® 445 provided stabilization without a rate decrease. The metal deactivators are expected to deactivate the catalyst, as was observed for Irganox® MD1024. The Naugard® XL-1 did not accomplish deactivation.

Example 8

Polymer Melt Stability as a Function of Moisture Content

Lactide, produced and purified in a continuous pilot plant, was fed at a rate of 3 kg/hr to a continuous polymerization pilot plant. Catalyst was added with a metering pump at the rate of 1 part catalyst to 5000 parts lactide on a molar basis. The reaction system was blanketed with nitrogen. The reactor vessels consist of two continuous stirred tank reactors (CSTR) in series. The first had a 1-gallon capacity and the second had a 5-gallon capacity. The reactors were run 60–80% liquid filled and at 170–180° C. Polymer melt pumps moved the liquid from CSTR 1 to CSTR 2, and from CSTR 2 through a die into a cooling water trough. The polymer strand thus produced was pulled from the trough by a pelletizer and stored as pellets.

The pelletized polylactide was put into a drying hopper and dried at 40° C. under flowing dry air. Samples were pulled after one hour and four hours. These samples were then run through a single screw Brabender® extruder, with a retention time of approximately 3 minutes. Samples were analyzed for moisture by an automatic Karl Fischer apparatus and for molecular weight by GPC (the method of Example 1). The results of these tests are documented in Table 13 below.

TABLE 13

| Sample | Extruder Temperature (C.) | Weight Average Molecular Weight |
|---|---|---|
| Initial | | 63,000 |
| Dried 1 hour | 137 | 44,000 |
| (1200 ppm $H_2O$) | 145 | 48,000 |

TABLE 13-continued

| Sample | Extruder Temperature (C.) | Weight Average Molecular Weight |
|---|---|---|
| | 162 | 35,000 |
| | 179 | 30,000 |
| Dried 4 hours | 140 | 63,000 |
| (150 ppm $H_2O$) | 140 | 69,000 |
| | 160 | 65,000 |
| | 178 | 68,000 |

These results show the detrimental effect of water in the lactide polymer resin during melt polymerization and the need to properly dry the polylactide before melt-processing.

Example 9

Degradation of Crystalline and Amorphous Polylactide

Two literature references disclose poly(D,L-lactide) to degrade faster than poly(L-lactide), attributing the result to crystallinity of poly(L-lactide). These are: Kulkarni et al., *J. Biomed. Mater. Res.*, vol. 5, pp. 169–181, (1971); Makino et al., *Chem. Pharm. Bull.*, vol. 33, pp. 1195–1201, (1985). An experiment was conducted to measure the effect of crystallinity on polymer degradation and is detailed below.

An amorphous polylactide sample (clear, and less than 1% crystallinity based on DSC) and a crystalline polylactide sample (opaque, and approximately 50% crystallinity based on DSC) were subjected to biodegradation in a compost test (50° C., with aeration). The DSC apparatus was a TA Instruments, Inc., model 910 differential scanning calorimeter with DuPont 9900 computer support system typically programmed to heating at a rate of 10° C. per minute to 200° C. The samples had different optical composition, with the crystalline sample being more than 90% poly(L-lactide) and the amorphous sample being less than 80% poly(L-lactide) with the balance being either poly(D,L-lactide) or poly (meso-lactide). Samples of each polymer were subjected to a compost test which included mixing a stabilized compost and providing a source of humidified air while maintaining a temperature of about 50° C. The amorphous sample was completely degraded after 30 days of composting. The crystalline sample was only 23% degraded based on carbon dioxide after the same period of time.

Additional samples of these two polymers were subjected to chemical hydrolysis at 50° C. (hydrolysis is believed to be the rate-limiting step in the biodegradation process). The chemical hydrolysis procedure included placing 0.1 gram polylactide in 100 ml of 0.2 M phosphate buffer (pH=7.4). The samples were held for 1 week, then filtered, washed with deionized water, and dried at 25° C. under vacuum. The initial weight average molecular weight for each sample was about 70,000. After 1 week the amorphous sample had a weight average molecular weight of 10,000 and the crystalline sample had a weight average molecular weight of 45,000, determined by GPC (the method of Example 1). Neither sample had significant weight loss at this time.

Both of these tests demonstrate that degradation of crystalline polylactide is slower than degradation of amorphous polylactide.

Example 10

Effect of Monomer Concentration on Film Modulus

Polylactide was precipitated in methanol from a chloroform solution in order to remove the residual lactide monomer. GPC analysis (the method of Example 1) showed the precipitated polymer to contain 0.0% lactide.

The polymer was dissolved in chloroform to make a 10 wt % solution, and lactide was added back to make 5 separate solutions which, after removing the chloroform, are calculated to produce films containing 0.0, 0.2, 0.4, 1.0 and 4.0 wt % lactide in polylactide. These solutions were solvent cast onto glass, dried overnight at room temperature in a fume hood, and removed to a vacuum oven. The films were hung in the vacuum oven and dried at 30° C. for 72 hours. GPC analysis of the vacuum-dried films showed measured lactide levels of 0.0, 0.0, 0.0, 0.7 and 3.7 wt %.

The films were then tested for film modulus using ASTM procedure D882.

The results are shown below in Table 14.

TABLE 14

| % Lactide | Tensile (psi avg.) | Std. Dev. | % Elongation | Std. Dev. | Elastic Modulus (psi. avg.) | Std. Dev. |
|---|---|---|---|---|---|---|
| 0 | 5490 | 636 | 2.85 | 0.14 | 730,000 | 103,000 |
| 0 | 6070 | 123 | 2.85 | 0.22 | 818,000 | 35,000 |
| 0 | 5670 | 227 | 2.75 | 0.27 | 779,000 | 44,000 |
| 0.7 | 5690 | 343 | 4.04 | 1.12 | 749,000 | 58,000 |
| 3.7 | 5570 | 458 | 3.33 | 1.43 | 738,000 | 66,000 |

Example 11

Rate of Water Uptake Versus Optical Composition

Samples of polylactide, made from 80% L-lactide and 20% of either D,L-lactide or meso-lactide, were ground to pass a 20 mesh screen. The samples were dried and devolatilized under vacuum then removed to a constant humidity chamber maintained at 24° C. and 50% relative humidity. The rate of moisture pick-up was determined gravimetrically, with the final results verified by Karl-Fischer water analysis. The rate of moisture pickup is shown below in Table 15.

TABLE 15

| Time | Parts Per Million Weight Gain | |
|---|---|---|
| (Minutes) | L/D,L Polymer | L/Meso Polymer |
| 10 | 600 | 1000 |
| 30 | 1100 | 1500 |
| 60 | 1500 | 1800 |
| 120 | 1600 | 2100 |
| 870 | 2100 | 2600 |
| Karl-Fischer | 3000 | 2600 |

Example 12

Standard Test of Melt Stability

A standard test for determining melt stability is as follows:

A small sample (200 grams or less) of polymer is ground or pelletized and devolatilized by holding under vacuum (about 10 mm Hg) at a temperature of 130° C. or less for 18 hours. At this point the residual lactide content should be 1 wt % or less. Portions (1–5 grams) of the devolatilized sample are then placed in a 16 ml sample vial, tightly capped, and placed in a 180° C. oil bath. Samples are removed at times of 15 minutes and 1 hour and analyzed for lactide content by GPC or other appropriate techniques. Lactide which may collect on the cooler portions of the vial is included in the product work-up and test.

Melt-stabilized polylactide will show less than 2% lactide in the 15 minute sample, and more preferably less than 2% lactide in the 1 hour sample. The most highly stabilized polylactides will maintain lactide contents of less than 1% in both the 15 minute and 1 hour samples, preferably less than 0.5%. An unstabilized polylactide may reach the equilibrium lactide content at 180° C. of 3.6 wt %, or may go even higher as lactide is driven from the polymer melt and collects on the cooler top walls of the vial.

Example 13

Water Scavenger Experiments

Dried polylactide pellets were processed in a twin screw extruder to devolatilize and to prepare a portion with 0.5 percent by weight of a water scavenger (Stabaxol® P). The strands leaving the extruder are cooled in a water trough and chopped into pellets. Samples of the control and the test sample were then analyzed by the Karl Fischer technique for moisture content, with no drying. The control sample contained 1700 ppm water, the test sample had 450 ppm water. The control sample was then dried under nitrogen at 40° C., reducing the water content to 306 ppm. A vacuum-dried control sample had 700 ppm water.

The as-produced test sample and the dried control samples were then processed in a ½" single screw extruder (Bradender®) at 160° C., with a retention time of 3 minutes. The number average molecular weight for the dried control sample dropped from an initial value of 44,000 to a final value of 33,000 for the 306 ppm water sample and to 28,000 for the 700 ppm water sample. The test sample number average molecular weight dropped from an initial value of 40,000 to a final value of 33,000.

This sample shows how the water scavenger protected the polymer from moisture pick-up, imparting the same stability as a thorough drying of the control sample. Combining a water scavenger with appropriate drying is expected to give even greater stability.

Example 14

Optimization of Catalyst Concentration

A mixture of 80% L-lactide and 20% D,L-lactide was polymerized using three different levels of tin(II) bis(2-ethyl hexanoate) catalyst. Batches were prepared at monomer/catalyst molar ratios of 1000:1, 3000:1, and 20,000:1. Polymerization times were adjusted to reach high conversion without being excessively long and thereby causing degradation in the melt. The reaction times were 1,2 and 20 hours, respectively. The polymerization temperature was 180° C. The polymers were ground to a coarse powder and devolatilized at 125° C. and 10 mm Hg overnight. The samples were then reground and 1-gram portions of each were placed into silanized vials, 16 ml capacity. The vials were sealed and placed into an oil bath at 180° C. Vials were then removed at various times and the samples were analyzed by GPC after dissolution in chloroform. The molecular weights and lactide-contents are shown below in Table 16.

TABLE 16

| Sample | Time (min) | Number Average Molecular Weight | Weight Average Molecular Weight | Lactide Weight % |
|---|---|---|---|---|
| 1000:1 | 0 | 39,000 | 81,300 | 0.8 |
|  | 5 | 28,100 | 57,300 | 2.4 |
|  | 15 | 25,800 | 49,700 | 2.8 |
|  | 30 | 23,100 | 43,800 | 3.7 |
|  | 60 | 22,800 | 43,200 | 3.6 |
| 3000:1 | 0 | 53,100 | 113,600 | 0.6 |
|  | 5 | 39,000 | 76,400 | 0.4 |
|  | 15 | 30,300 | 65,400 | 1.9 |
|  | 30 | 29,000 | 60,400 | 2.7 |
|  | 60 | 28,200 | 55,200 | 2.8 |
| 20000:1 | 0 | 89,200 | 184,000 | 0.0 |
|  | 5 | 81,200 | 165,100 | 0.0 |
|  | 15 | 54,300 | 134,600 | 0.1 |
|  | 30 | 51,100 | 119,600 | 0.0 |
|  | 60 | 49,500 | 111,000 | 0.0 |

These results show the benefit of optimizing the catalyst level used in the polymerization process. Note that both lactide reformation and molecular weight retention benefits are realized from the reduced catalyst levels (higher monomer/catalyst ratio).

It is believed catalyst levels should be limited to 1000:1 for the high end of catalyst usage, with 3000:1 being more preferable and showing somewhat improved stability. Lower levels still, such as 20000:1, show greatly improved stability. Beyond this level it is believed the polymerization rates become too slow to be practical.

Example 15

Removal of Tin Catalyst from Polylactide by Precipitation 45 grams of L-lactide and 13 grams of D,L-lactide were charged with 78 milligrams of crystalline lactic acid to a 200 ml round bottom flask. This was heated to 180° C. with magnetic stirring in an oil bath and blanketed with dry nitrogen. Catalyst in the form of tin(II) bis(2-ethyl hexanoate) was added as 0.20 ml of a 0.47 g/ml solution in THF after the molten lactide was at temperature. The mixture was allowed to stir for one minute and then pipetted into 3 silanized glass vials, which were then sealed and placed into a 180° C. oil bath for 75 minutes. The vials were allowed to cool and the polymer recovered by breaking the glass. The polymer was ground to a coarse powder and dissolved in chloroform to make a 10% solution. The polymer contained 3.8% residual monomer and had a number average molecular weight of 70,000 as determined by GPC measurement (the method of Example 1).

500 ml of methanol were placed in a 1-liter glass blender flask. The blender was turned on to medium speed and 50 ml of the polymer in chloroform solution was poured in over a period of three minutes. After one additional minute of blending the mixture was filtered, then rinsed with 100 ml of methanol, and dried overnight under vacuum. The polymer consisted of a fibrous mat. It contained 0.3% residual monomer and had a number average molecular weight of 66,900.

The measured tin level in the precipitated polymer was 337 ppm. by weight, compared to a calculated value of 466 ppm for the as-produced polymer. This result indicates the feasibility of reducing residual catalyst levels in lactide polymers by solvent precipitation with the benefit of improved stability as detailed in Example 14.

Example 16

Melt-Processability Versus Molecular Weight and Viscosity

The Melt Flow Index (MI) is specified by ASTM method D-1238 and is frequently used as a practical measure of viscosity for processing applications. Higher melt flow index corresponds to lower viscosity. Desired values of the melt flow index range from 0.1–2 for a typical extrusion operation, 10–20 for film extrusion or for paper coating, and 1–10 for injection molding.

Based on capillary viscometer measurements the applicants have estimated melt flow index as a function of temperature and molecular weight, with results shown below in Table 17.

TABLE 17

| Number Average Molecular Weight | Weight Average Molecular Weight | Melt Flow Index (Calc) | | |
|---|---|---|---|---|
| | | @ 150° C. | @ 175° C. | @ 200° C. |
| 50,000 | 100,000 | 75 | 1600 | 36000 |
| 75,000 | 150,000 | 18 | 400 | 9000 |
| 100,000 | 200,000 | 6 | 140 | 3000 |
| 150,000 | 300,000 | 1.5 | 34 | 800 |
| 200,000 | 400,000 | 0.6 | 13 | 300 |
| 250,000 | 500,000 | 0.3 | 6 | 120 |
| 300,000 | 600,000 | 0.1 | 3 | 70 |

High temperature processing of polylactide is undesirable because both lactide reformation and molecular weight reductions become more severe as temperature increases. The effect of temperature on degradation is shown, for example, by Jamshidi et al., *Polymer,* vol. 29, pp. 2229–2234 (1988), incorporated herein by reference, and detailed in prior experimental examples. Acceptable temperature ranges vary with the stability of the polymer and the processing temperature.

The table above indicates that for unstabilized polymers, which might be processed at 150° C., an upper limit of 100,000 for the number average molecular weight would be appropriate to achieve a melt flow index near 10 (as might be used for injection molding). For slightly stabilized polymers, which could be processed at 175° C. without degradation or lactide reformation, the number average molecular weight could be as high as 250,000 with a weight average molecular weight of 500,000. For the most stabilized polymers, which could be processed at 200° C. or higher, the molecular weight will be limited only by purity of the lactide. Applications which can operate at lower melt flow indices will have greater tolerance for higher molecular weight.

Note that these processing temperatures are approximations for post-processing, and that the devolatilization operation will frequently be carried out at higher temperatures in order to effectively remove the lactide.

It will be understood, however, that even though these numerous characteristics and advantages of the invention have been set forth in the foregoing description, together with details of the structure and function of the invention, the disclosure is illustrative only, and changes may be made in detail, especially in matters of shape, size and arrangement of the parts or in the sequence or the timing of the steps, within the broad principle of the present invention to the full extent indicated by the broad general meaning of the terms in which the appended claims are expressed.

What is claimed is:

1. A method for producing devolatilized polylactide polymer composition comprising:

(a) providing a polylactide polymer composition comprising polylactide, lactide, and polylactide polymerization catalyst, wherein the polylactide polymer composition has a number average molecular weight between about 10,000 and about 300,000;

(b) adding a stabilizing agent to said polylactide polymer composition; and (c) devolatilizing said polylactide polymer composition containing stabilizing agent to remove at least a portion of said lactide to provide a polylactide polymer composition including less than about 2 percent by weight lactide.

2. A method for producing devolatilized polylactide polymer composition according to claim 1, wherein said polylactide polymer composition has a number average molecular weight of between about 15,000 and about 150,000.

3. A method for producing devolatilized polylactide polymer composition according to claim 1, wherein said polylactide polymer composition is a result of polymerizing lactide mixture at a temperature greater than 160° C. in the presence of a polylactide polymerization catalyst, wherein the molar ratio of lactide to catalyst is greater than 5,000:1.

4. A method for producing devolatilized polylactide polymer composition according to claim 1, wherein the polylactide polymerization catalyst comprises a tin containing catalyst.

5. A method for producing devolatilized polylactide polymer composition according to claim 1, wherein said stabilizing agent is selected from the group consisting of antioxidants, water scavengers, catalyst deactivators, and mixtures thereof.

6. A method for producing devolatilized polylactide polymer composition according to claim 3, further comprising adding a molecular weight control agent to said lactide mixture prior to polymerizing in the presence of a polylactide polymerization catalyst.

7. A method for producing devolatilized polylactide polymer composition according to claim 6, wherein said molecular weight control agent is selected from the group consisting of lactic acid, asterlactic acid, alcohols, amines, glycols, diols, and triols.

8. A method for producing devolatilized polylactide polymer composition according to claim 1, wherein said stabilizing agent is a phosphite stabilizer.

9. A method for producing devolatilized polylactide polymer composition according to claim 1, wherein the step of devolatilizing comprises devolatilizing to provide a stabilized polylactide polymer composition containing less than 0.5% by weight lactide, based on the total weight of the composition.

10. A method for producing devolatilized polylactide polymer composition according to claim 1, further comprising providing said stabilized polylactide polymer composition in a pelletized or granular form.

11. A method for producing devolatilized polylactide polymer composition according to claim 1, wherein said stabilizing agent comprises phenolic antioxidant.

12. A method for producing devolatilized polylactide polymer composition according to claim 1, further comprising melt processing said stabilized polylactide polymer composition into a film, packaging material, molded article, or nonwoven.

13. A method for producing devolatilized polylactide polymer composition according to claim 1, further comprising melt processing said stabilized polylactide polymer composition to provide a coating on paper.

14. A method for producing devolatilized polylactide polymer composition comprising:

(a) providing a lactide mixture comprising lactide and phosphite containing stabilizing agent;

(b) adding a polylactide polymerization catalyst to said lactide mixture;

(c) polymerizing said lactide mixture at a temperature greater than about 160° C. to form composition comprising polylactide, lactide, polylactide polymerization catalyst, and phosphite stabilizing agent; and (d) devolatilizing to remove at least a portion of said lactide.

15. A method for producing devolatilized polylactide polymer composition according to claim 14, wherein said polylactide polymer composition has a number average molecular weight of between about 15,000 and about 150,000.

16. A method for producing devolatilized polylactide polymer composition according to claim 14, wherein said polylactide polymer composition is a result of polymerizing lactide at a temperature greater than 160° C. in the presence of a polylactide polymerization catalyst, wherein the molar ratio of lactide to catalyst is greater than 5,000:1.

17. A method for producing devolatilized polylactide polymer composition according to claim 14, wherein the polylactide polymerization catalyst comprises a tin containing catalyst.

18. A method for producing devolatilized polylactide polymer composition according to claim 14, further comprising adding a molecular control agent to the lactide mixture prior to polymerizing said lactide mixture.

19. A method for producing devolatilized polylactide polymer composition according to claim 18, wherein said molecular weight control agent is selected from the group consisting of lactic acid, asterlactic acid, alcohols, amines, glycols, diols, and triols.

20. A method for producing devolatilized polylactide polymer composition according to claim 14, wherein the step of devolatilizing comprises devolatilizing to provide a stabilized polylactide polymer composition containing less than 0.5% by weight lactide, based on the total weight of the composition.

21. A method for producing devolatilized polylactide polymer composition according to claim 14, further comprising providing said stabilized polylactide polymer composition in a pelletized or granular form.

22. A method for producing devolatilized polylactide polymer composition according to claim 14, wherein said stabilizing agent comprises phenolic antioxidant.

23. A method for producing devolatilized polylactide polymer composition according to claim 14, further comprising melt processing said stabilized polylactide polymer composition into a film, packaging material, molded article, or nonwoven.

24. A method for producing devolatilized polylactide polymer composition according to claim 14, further comprising melt processing said stabilized polylactide polymer composition to provide a coating on paper.

* * * * *

UNITED STATES PATENT AND TRADEMARK OFFICE
CERTIFICATE OF CORRECTION

PATENT NO. : 5,981,694
DATED : NOVEMBER 9, 1999
INVENTOR(S) : GRUBER ET AL.

It is certified that error appears in the above-identified patent and that said Letters Patent is hereby corrected as shown below:

Front page, [75] Inventors: "St. Paul" should read --Blaine--

Col. 15, line 56: "waters" should read --Waters--

Col. 17, line 3 of Table 2: "Initial" should be moved down to line 4

Col. 17, lines 2-3 of Table 2: "Molecular Weight After" should be moved down to lines 3-4

Col. 18, line 64: "Fascat" should read --Fascat®--

Col. 23, line 31, Table 9: "65,500" should read --66,500--

Signed and Sealed this

Seventeenth Day of April, 2001

*Attest:*

NICHOLAS P. GODICI

*Attesting Officer*      *Acting Director of the United States Patent and Trademark Office*